(12) United States Patent
Ragosta

(10) Patent No.: US 11,653,912 B2
(45) Date of Patent: May 23, 2023

(54) NEEDLE DRIVER DEVICES AND RELATED SYSTEMS AND METHODS

(71) Applicant: INTUITIVE SURGICAL OPERATIONS, INC., Sunnyvale, CA (US)

(72) Inventor: Nicholas Ragosta, San Francisco, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 101 days.

(21) Appl. No.: 17/118,746

(22) Filed: Dec. 11, 2020

(65) Prior Publication Data

US 2021/0177399 A1 Jun. 17, 2021

Related U.S. Application Data

(60) Provisional application No. 62/947,081, filed on Dec. 12, 2019.

(51) Int. Cl.
*A61B 17/062* (2006.01)
*A61B 17/04* (2006.01)
*A61B 17/06* (2006.01)

(52) U.S. Cl.
CPC ........ *A61B 17/062* (2013.01); *A61B 17/0482* (2013.01); *A61B 17/06066* (2013.01)

(58) Field of Classification Search
CPC .......... A61B 17/062; A61B 2017/0608; A61B 17/0482; A61B 17/06066; A61B 34/70
See application file for complete search history.

(56) References Cited

U.S. PATENT DOCUMENTS

| 7,862,572 | B2 | 1/2011 | Meade et al. |
| 7,976,555 | B2 | 7/2011 | Meade et al. |
| 7,993,354 | B1 | 8/2011 | Brecher et al. |
| 8,066,737 | B2 | 11/2011 | Meade et al. |
| 8,123,764 | B2 | 2/2012 | Meade et al. |
| 8,469,973 | B2 | 6/2013 | Meade et al. |

(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Kathleen S Holwerda
*Assistant Examiner* — Serenity A Miller
(74) *Attorney, Agent, or Firm* — Jones Robb, PLLC

(57) ABSTRACT

A needle driver device includes an arc-shaped track and an arc-shaped needle configured to be received in the arc-shaped track. The arc-shaped needle is moveable along a curved path including the arc-shaped track. The needle driver device further includes a rotary drive mechanism and a needle driver link. The needle driver link has a distal end portion configured to removably engage the arc-shaped needle and a proximal end portion coupled to the rotary drive mechanism. The needle driver device also includes a guide member coupled to the needle driver link and defining a pivot location of the needle driver link between the distal end portion and the proximal end portion of the needle driver link. The needle driver link is rotatable about the pivot location, and the guide member is moveable in response to movement of the needle driver link.

15 Claims, 13 Drawing Sheets

(56) References Cited

U.S. PATENT DOCUMENTS

| | | |
|---|---|---|
| 8,821,519 B2 | 9/2014 | Meade et al. |
| 8,852,208 B2 | 10/2014 | Gomez et al. |
| 9,358,074 B2 | 6/2016 | Schena et al. |
| 9,451,948 B2 | 9/2016 | Meade et al. |
| 9,474,523 B2 | 10/2016 | Meade et al. |
| 9,486,209 B2 | 11/2016 | Martin et al. |
| 9,597,071 B1 | 3/2017 | Meade et al. |
| 9,642,613 B1 | 5/2017 | Meade et al. |
| 9,642,614 B1 | 5/2017 | Meade et al. |
| 9,662,104 B1 * | 5/2017 | Nobles ............. A61B 17/06066 |
| 9,675,339 B2 | 6/2017 | Brecher et al. |
| 9,700,301 B2 | 7/2017 | Meade et al. |
| 9,700,302 B2 | 7/2017 | Meade et al. |
| 9,775,600 B2 | 10/2017 | Brecher et al. |
| 9,795,376 B2 | 10/2017 | Meade et al. |
| 9,795,377 B2 | 10/2017 | Meade et al. |
| 9,808,238 B2 | 11/2017 | Meade et al. |
| 9,936,944 B2 | 4/2018 | Meade et al. |
| 9,962,151 B2 | 5/2018 | Brecher et al. |
| 9,962,153 B2 | 5/2018 | Meade et al. |
| 9,962,154 B2 | 5/2018 | Meade et al. |
| 9,962,155 B2 | 5/2018 | Meade et al. |
| 9,962,156 B2 | 5/2018 | Meade et al. |
| 9,986,997 B2 | 6/2018 | Meade et al. |
| 10,098,630 B2 | 10/2018 | Meade et al. |
| 10,111,654 B2 | 10/2018 | Meade et al. |
| 10,292,698 B2 | 5/2019 | Meade |
| 10,307,155 B2 | 6/2019 | Meade et al. |
| 10,383,622 B2 | 8/2019 | Meade et al. |
| 10,792,031 B2 | 10/2020 | Brecher et al. |
| 10,792,032 B2 | 10/2020 | Meade et al. |
| 10,881,392 B2 | 1/2021 | Brecher et al. |
| 11,033,262 B2 | 6/2021 | Meade et al. |
| 11,039,829 B2 | 6/2021 | Meade |
| 11,253,249 B2 | 2/2022 | Meade et al. |
| 11,253,250 B2 | 2/2022 | Meade |
| 2006/0069396 A1 * | 3/2006 | Meade ............... A61B 17/0482 606/144 |
| 2015/0133967 A1 * | 5/2015 | Martin ............... A61B 17/0625 606/144 |
| 2021/0298744 A1 | 9/2021 | Meade et al. |

* cited by examiner

NEEDLE DRIVER DEVICES AND RELATED SYSTEMS AND METHODS

CROSS-REFERENCE TO RELATED APPLICATIONS

This application claims priority to U.S. Provisional Application No. 62/947,081 (filed Dec. 12, 2019), titled "NEEDLE DRIVER DEVICES AND RELATED SYSTEMS AND METHODS," the entire contents of which are incorporated by reference herein.

TECHNICAL FIELD

Aspects of the present disclosure relate to devices, systems, and methods for performing a suturing procedure. For example, aspects of the present disclosure relate to needle driver devices including, but not limited to, for example, devices configured to insert sutures during remote surgical, diagnostic, therapeutic, and other treatment procedures. Further aspects of the disclosure relate to methods of operating such devices.

INTRODUCTION

Sutures are used in a variety of surgical and other applications, such as closing ruptured or incised tissue, soft tissue attachment, attachment of grafts, etc. Additionally, sutures may have other medical and/or non-medical uses. Conventionally, suturing is accomplished by penetrating tissue with the sharpened tip of a suturing needle that has a thread of suturing material attached to the opposite blunt end of the needle. The needle is then pulled through the tissue, causing the attached thread of suturing material to follow the path of the needle. Typically, a knot is tied at the trailing end of the thread to anchor the first stitch. This action is performed repetitively with application of tension to the needle to pull a length of the thread through the tissue using subsequent stitches until the tissue is sutured as desired with one or more stitches.

While the above-described suturing process can be performed manually, automated suturing systems also exist. Such systems can include a needle driver device that has an open, C-shaped portion into which tissue segments are introduced. The C-shaped portion defines two arms, each with an entry/exit point for a curved needle. The curved needle is driven around a track (generally following the C-shaped portion) and across the opening in the C-shaped portion to draw a thread of suturing material into the needle driver device through the tissue segments, similar to the manual suturing process discussed above. It is desirable to provide needle driver devices that occupy a minimal amount of space relative to a size (e.g., gauge and/or radius) of the needle. Such tools are useful in space-limited applications, such as in the case of minimally invasive surgery, for example laparoscopic surgery including both manual and computer-assisted surgery.

A need exists to provide needle driver devices with an overall relatively small working end. A need also exists to provide robust mechanical parts and operational design of such devices to reduce complexity and/or wear on parts of the device. A further need exists to provide such devices with a greater level of reliability in use and manufacturability, which can contribute to low overall cost of use during a lifetime of the device.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one aspect of the present disclosure, a needle driver device includes an arc-shaped track and an arc-shaped needle configured to be received in the arc-shaped track. The arc-shaped needle is moveable along a curved path including the arc-shaped track. The needle driver device further includes a rotary drive mechanism and a needle driver link. The needle driver link has a distal end portion configured to removably engage the arc-shaped needle and a proximal end portion coupled to the rotary drive mechanism. The needle driver device also includes a guide member coupled to the needle driver link and defining a pivot location of the needle driver link between the distal end portion and the proximal end portion of the needle driver link. The needle driver link is rotatable about the pivot location, and the guide member is moveable in response to movement of the needle driver link.

In accordance with at least another aspect of the present disclosure, a needle driver device includes an arc-shaped track and an arc-shaped needle configured to be received by the arc-shaped track. The arc-shaped needle is moveable along a path including the arc-shaped track. The needle driver device includes a rotary drive mechanism and a needle driver link. The needle driver link includes a distal end portion removably engageable with the arc-shaped needle and configured to be removably coupled to the arc-shaped track. The needle driver link also includes a proximal end portion coupled to the rotary drive mechanism.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure and are incorporated in and constitute a part of this specification. The drawings illustrate one or more embodiments of the present teachings and together with the description explain certain principles and operation. In the drawings.

DETAILED DESCRIPTION

The present disclosure provides various embodiments of needle driver devices, systems, and methods. Needle driver devices according to various embodiments of the present disclosure include features that kinematically constrain movement of an end portion (such as a distal end portion) of a needle driver link, to which the needle is coupled, to follow a desired path, such as along an arc of a circular path. In various configurations, the motion of the needle driver link can be constrained without occupying undue space in the distal portion of the needle driver device, thus enabling a smaller overall size of the device for a given needle size.

In some exemplary embodiments, movement of an end portion (such as a proximal end portion) of the needle driver link opposite the end portion to which the needle is coupled, also can be constrained within a desired path. The path to which the proximal end portion of the needle driver link is constrained can be chosen such that, in combination with other constraining features, the distal end portion of the needle driver link is constrained to move along a portion of a curved (e.g., circular) path within the distal end portion of the needle driver device and to drive the needle with a desired motion. For example, in some embodiments, the needle may be driven in full rotations or partial rotations around the needle track and opening of the needle driver device to carry out a suturing process in response to input at a drive mechanism, as will be explained further below. In some exemplary embodiments, movement of the distal end portion of the needle driver link itself is constrained to a desired path, such as a circular path, by features of the distal end portion of the needle driver link that directly interface with features in the distal portion of the needle driver device. Such features can be configured so that they occupy minimal space within the distal portion of the needle driver device, thereby contributing to a small overall size of the needle driver device for a given needle size. In addition to reducing space requirements, these features can also contribute to reduced assembly and operational complexity, and to improved reliability and useful life of the device.

In some exemplary embodiments, a portion of the needle driver link between the proximal and distal ends can be constrained along multiple degrees of freedom. In combination with other constraints on the proximal and/or distal end of the needle driver link, the multiple degrees of freedom permit the proximal end to move along a first path, for example, a path defined by a drive mechanism of the needle driver device, and concurrently control the distal end portion of the needle driver link to move in a desired path, such as along a needle track, which in various embodiments may be circular.

Figure 1:
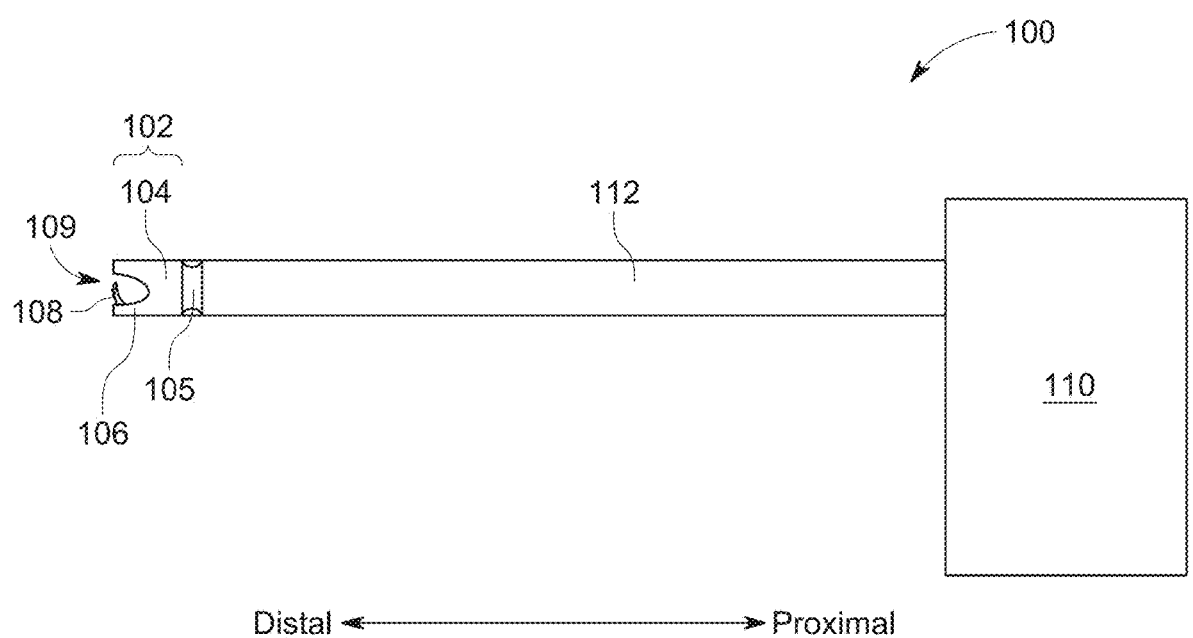
FIG. 1 is a schematic side view of an embodiment of a needle driver device.

Referring now to FIG. 1, a schematic view of a needle driver device 100 according to an exemplary embodiment of the disclosure is shown. The needle driver device 100 includes an end effector 104 at a distal end portion 102 of a shaft 112. The end effector 104 comprises a C-shaped portion 106, which houses an arc-shaped needle 108 (a sharpened tip portion of which is illustrated). In an exemplary embodiment, the needle 108 has a curvature corresponding to a circular arc. A transmission mechanism 110 is coupled to a proximal end portion of the shaft 112. The transmission mechanism 110 can be configured to be operably coupled with a computer-controlled (e.g., teleoperated) surgical manipulator system, such as the manipulator systems described below in connection with FIGS. 12 and 13, or it can be manually controlled with manually operated (e.g., handheld) actuators (not shown). The end effector 104 can optionally be coupled to the shaft 112 by a joint structure 105, such as a wrist, imparting one or more degrees of freedom to the end effector 104 relative to the shaft 112.

Drive inputs received at the transmission mechanism 110, whether through manual actuation or via a manipulator system, can actuate the end effector 104, such as by driving the needle 108 around a path defined partly by the C-shaped portion 106. Movement of the needle 108 across the opening 109 of the C-shaped portion 106 can be used to, for example, suture tissue or other materials positioned within the opening 109 of the C-shaped portion 106. For example, in some exemplary embodiments, the C-shaped portion 106 includes an arc-shaped needle track, as discussed further below, exhibiting a radius of curvature similar to a radius of curvature of the needle 108, and the needle 108 rotates about a center of curvature of the arc-shaped track.

The transmission mechanism 110 can include one or more drive components configured to receive an oscillating, rotational drive input from the drive mechanism, and to transmit the rotational drive input through an actuation member, such as, for example, a cable or rod (not shown) located within the shaft 112 and coupled at opposite ends to the transmission mechanism 110 and the end effector 104. In one exemplary embodiment, the actuation member can be a cable drive element having a pull/pull configuration. That is, the actuation member comprises a looped cable or two cables that can alternatingly be tensioned to achieve the desired drive motion. Various components within the end effector 104 can be configured to change the rotational, oscillating drive motion to a stepwise rotational motion of the needle 108, as discussed in connection with the exemplary embodiments described in connection with FIGS. 2-11.

Figure 2:
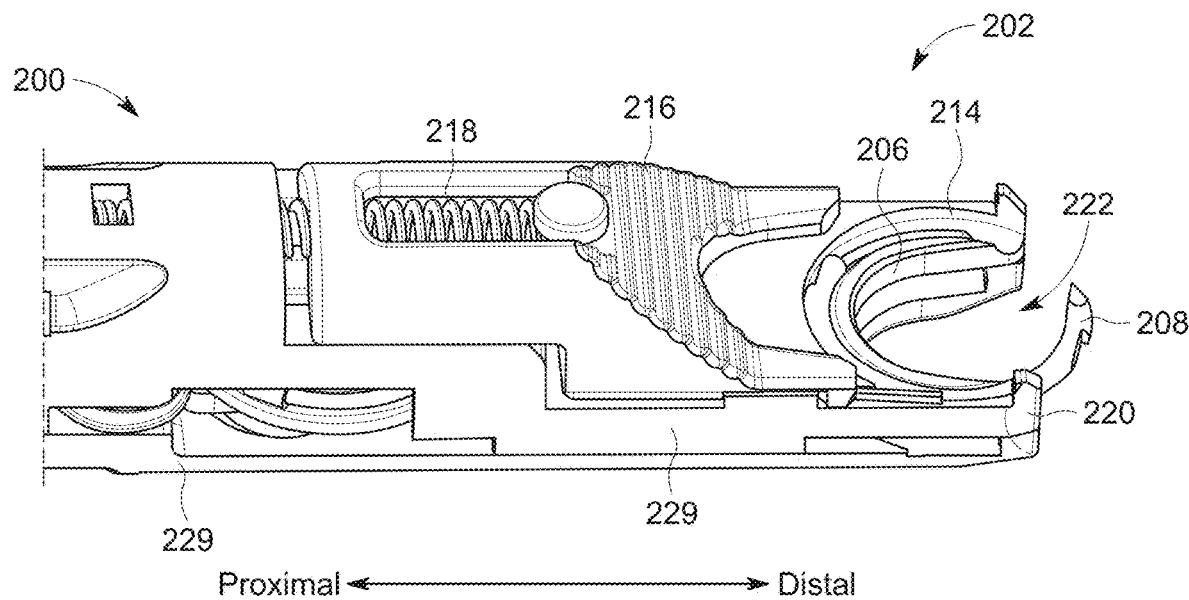
FIG. 2 is a perspective view of a distal portion of an embodiment of a needle driver device according to an exemplary embodiment of the present disclosure.

FIG. 2 shows one exemplary embodiment of a distal end portion 202 of a needle driver device 200 according to the present disclosure. The distal end portion 202 has a C-shaped portion 206 in which a needle track 214 is located. The needle track 214 receives an arc-shaped needle 208 and allows the needle 208 to travel along it. The distal end portion 202 further comprises a needle retainer 216 that is biased by a spring 218 to a normally closed position that can be retracted, against the biasing force, by a user to the open position illustrated in FIG. 2 to expose the needle 208 within the needle track 214. When not held in the retracted position, the needle retainer 216 is urged distally by spring 218 against stops 220 at distal edges of the distal end of the C-shaped portion 206 and covers the needle track 214. Exposure of the needle 208 by retraction of the needle retainer 216 permits replacement of the needle 208 and/or suture thread. In use during a suturing procedure, the needle retainer 216 remains in the closed position.

Figure 14A:
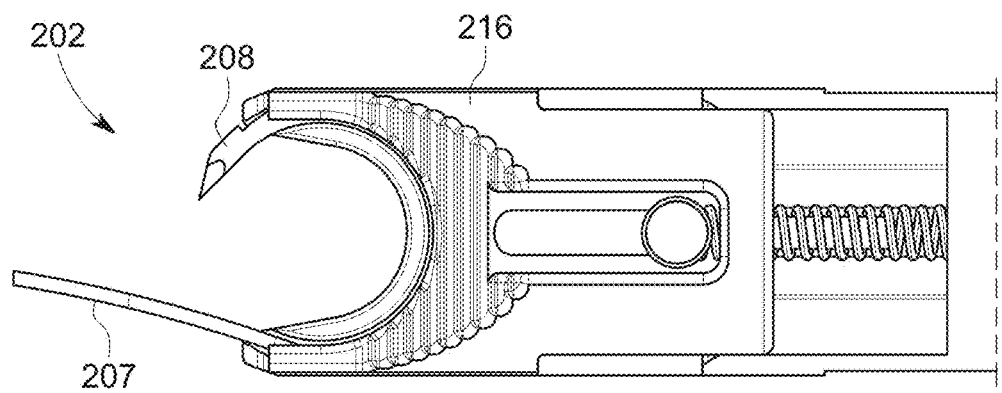
FIG. 14A is a top view of the needle driver device of FIG. 2 including a needle and suture material, with a needle retainer in a closed position.
Figure 14B:
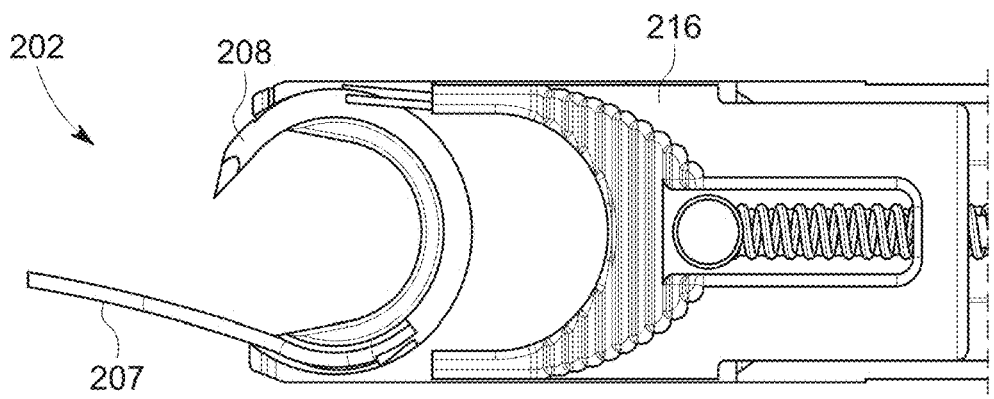
FIG. 14B is a top view of the needle driver device of FIG. 14A with the needle retainer in an open position.
Figure 14C:
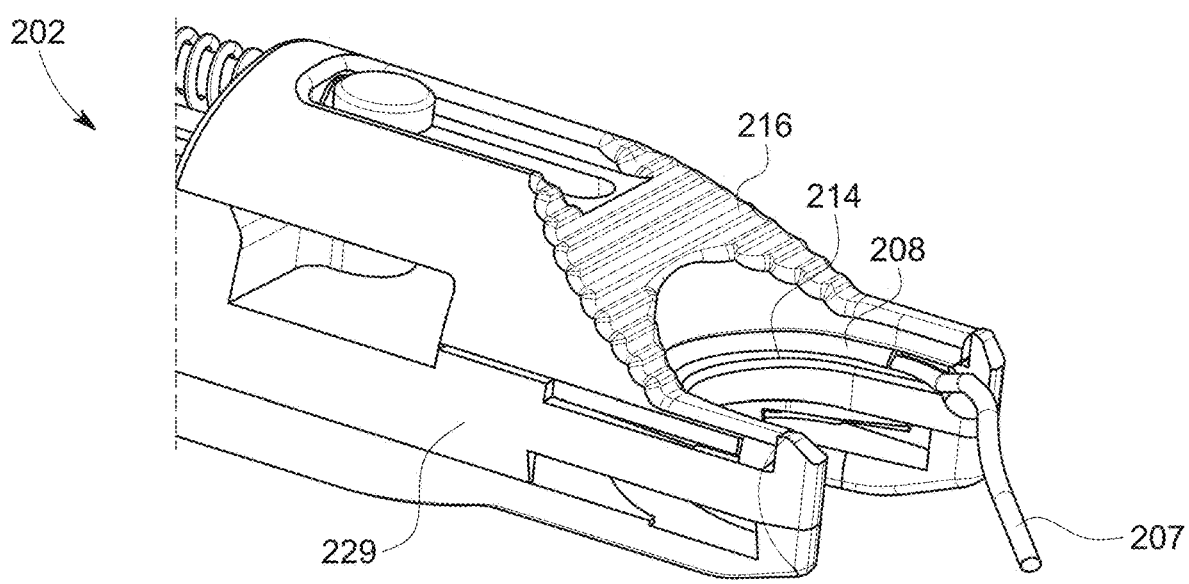
FIG. 14C is perspective view of the needle driver device of FIG. 14A with the needle retainer in the closed position.

The needle 208 can be driven around the needle track 214 in a cyclical manner. Each complete rotation (i.e., 360-degree rotation) of the needle 208 can complete a single suture stitch in the tissue or other material positioned in the C-shaped portion of the needle driver device 200. In exemplary embodiments, the thread of suture material can be coupled (e.g., tied) at a leading or trailing portion of the needle 208, and the thread can follow the needle 208 through the needle track 214 as the needle 208 rotates to complete each suture. FIGS. 14A-14C show views of the distal end portion 202 of the needle driver device with suture material 207 attached to a trailing portion of the needle 208. FIG. 14A shows the needle retainer 216 in the closed position. FIG. 14B shows the needle retainer 216 in the open position to reveal the suture material 207 attached to the trailing portion of the needle. It should be appreciated, however, that in normal use, the needle retainer 216 would be in the closed position to conduct the suturing procedure. FIG. 14C shows a perspective view of the distal end portion 202 of the needle driver device with the needle retainer 216 in the closed position. In the closed position of the needle retainer 216, a clearance exists between the needle retainer 216 and the needle track 214, which is formed in a portion of a housing 229 (see FIGS. 2-4) of the needle driver device. The needle retainer 216 retains the needle 208 in the track 214 as it rotates, while the attached suture material 207 is drawn through the clearance between the needle retainer 216 and the needle track 214.

Needle driver devices according to various embodiments of the present disclosure include drive components to rotate the needle through a full rotation, which can occur in a step-wise manner, without mechanical drive components entering a suturing area defined by the opening of the C-shaped portion. As described further below, such needle driver devices include various components that receive input from the transmission mechanism to actuate movement of the needle. In exemplary embodiments, the transmission mechanism is coupled to a rotary drive mechanism, such as for example, a pulley, in the distal end portion of the needle driver device via a drive member, such as a cable or belt, extending from the transmission mechanism and through the shaft to the distal end portion of the needle driver device. Additional drive components convert oscillating rotational movement of the rotary drive mechanism into a reciprocating movement of another drive component along a desired path. These drive components can include features that removably couple with the needle such that the reciprocating movement of a drive component removably coupled with the needle drives the needle to rotate, including, for example, in a stepwise manner.

Figure 3:
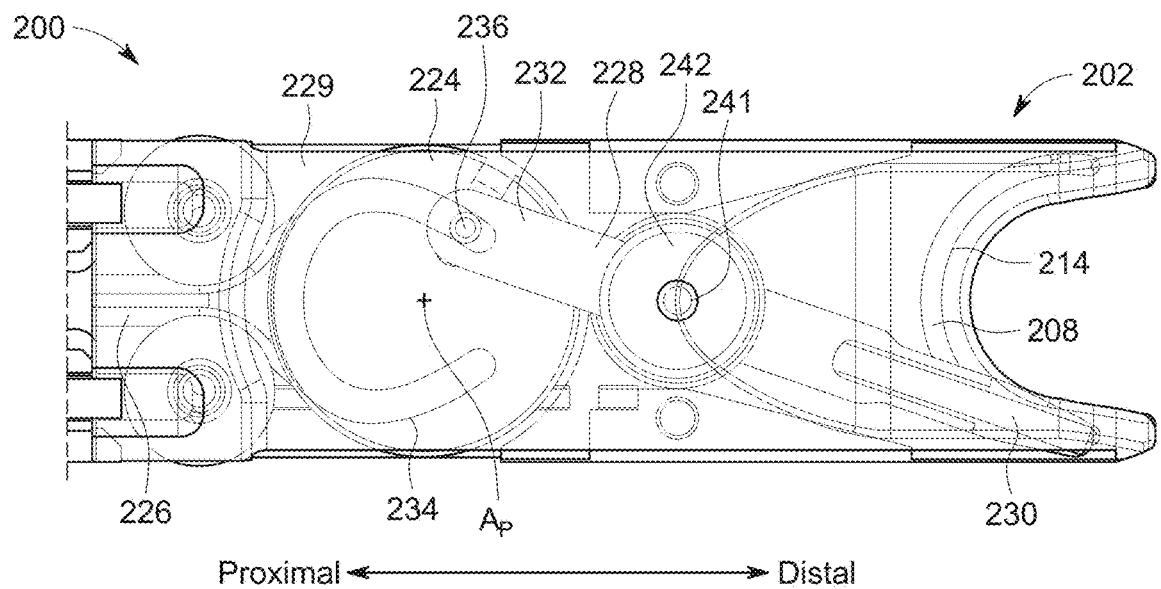
FIG. 3 is a top view of the needle driver device, with interior components depicted, of FIG. 2.
Figure 4:
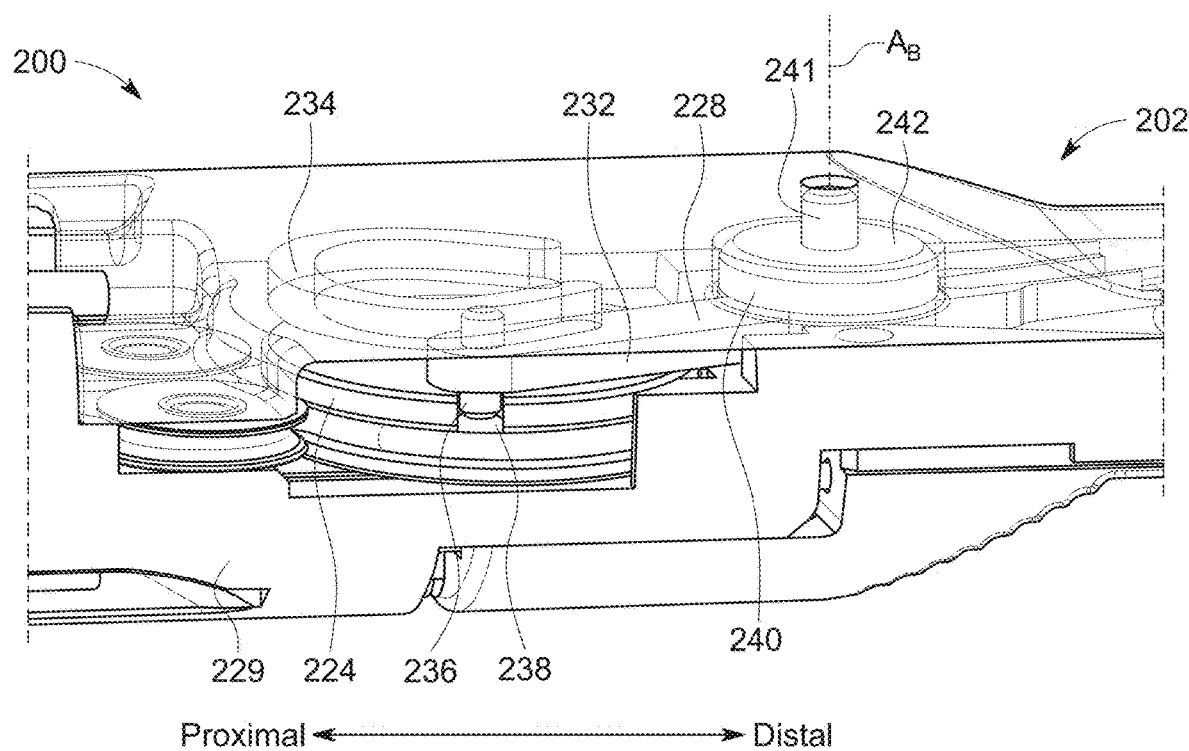
FIG. 4 is an enlarged perspective view of the needle driver device, with interior components depicted, according to the embodiment of FIG. 2.
Figure 5:
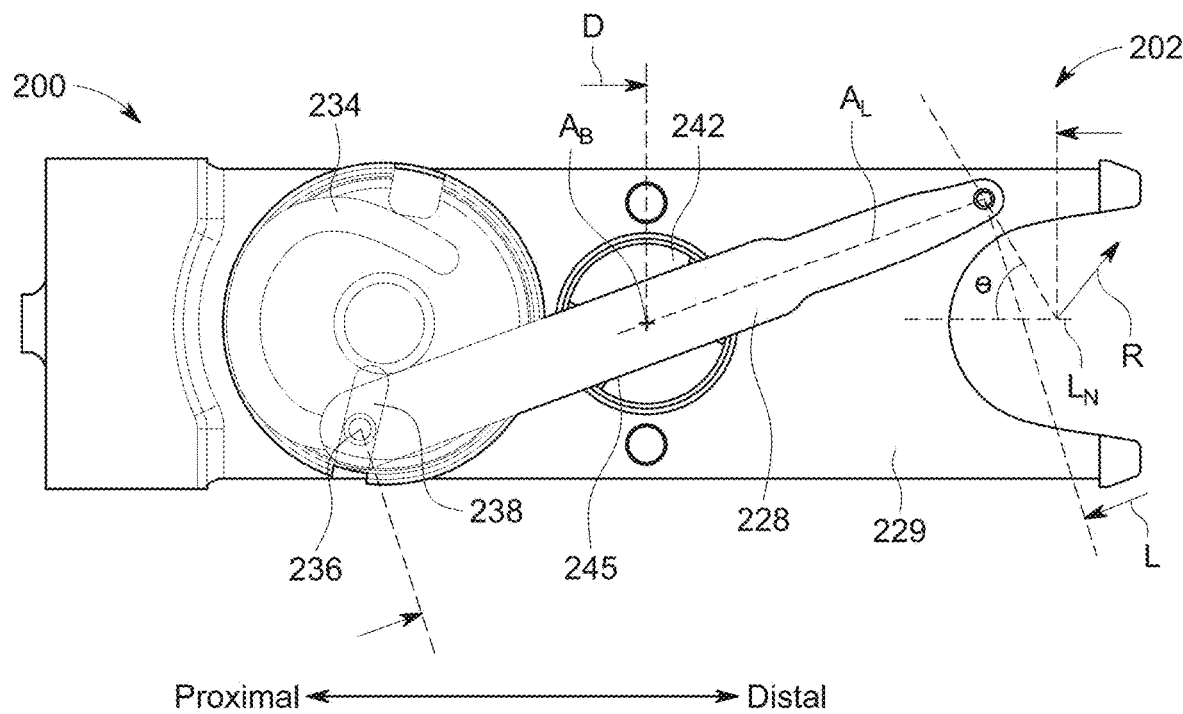
FIG. 5 is a top view of the needle driver device according to the embodiment of FIG. 2 with various interior components depicted to highlight aspects of the device.

FIGS. 3-5 show additional views of various drive system components and the operation of those components during use of the needle driver device 200 of FIG. 2. Referring now to FIG. 3, a top view of the needle driver device 200 is shown, with housing features omitted to display interior components of the drive system. The drive system of the needle driver device 200 includes a rotary drive mechanism in the form of a pulley drive assembly comprising a pulley disc 224 around which a drive member 226 extends. While the drive member 226 in FIG. 3 is illustrated as a belt, other continuous or non-continuous drive members, such as belts, cables, rods, or other members can be used, as would be readily appreciated by one having ordinary skill in the art. The drive member 226 can extend through the shaft 112 (FIG. 1) from the transmission mechanism 110 (FIG. 1) to the distal end portion 202 of the needle driver device 200. In some exemplary embodiments, the drive member 226 is operably coupled to a drive component (e.g., a capstan) (not shown) in the transmission mechanism (e.g., transmission mechanism 110), and operation of the manipulator (such as manipulator systems shown and described in connection with FIGS. 12 and 13, or a manual manipulator) actuates the drive component, placing tension on the drive member 226 to cause it to rotate the pulley disc 224.

While a pulley drive assembly is shown and described as the rotary drive mechanism in the embodiment of FIGS. 3-11, the rotary drive mechanism is not limited to a pulley drive assembly and can include other drive mechanisms to cause the rotary motion of rotary drive mechanism. By way of nonlimiting example, those of ordinary skill in the art would appreciate that a direct drive mechanism could be used to rotate the rotary drive mechanism, such as by using a motorized or other rotating shaft mechanism coupled to impart rotary motion to the rotary drive mechanism, a gear train, or any other mechanical or electro-mechanical drive-train.

Referring again to FIG. 3, the pulley disc 224 is operably coupled with a needle driver link 228 that extends generally distally from the pulley disc 224 and terminates at the distal end portion 202. The driver link 228 removably engages with the needle 208 at a distal end portion 230 of the driver link 228, which is described in further detail below in connection with FIGS. 6A-6I. The motion of the distal end portion 230 is constrained to follow the arc defined by the needle track 214. However, in the exemplary embodiment of FIGS. 2-5, the distal end portion 230 of the driver link 228 is not physically constrained by way of engagement within or adjacent to the needle track 214. Instead, other portions of the driver link 228 are constrained by various components of the drive system, which ensures that the motion of the distal end portion 230 of the driver link 228 follows the arc of the needle track 214. This can enable a smaller overall size of the needle driver device 200.

As shown in FIG. 3, motion of a proximal end portion 232 of the driver link 228 also is constrained by components of the drive system. A housing 229 (shown in FIG. 2 and partly in ghost in FIG. 4; not shown in FIG. 3 to reveal interior components of the needle driver device 200) includes on an interior surface a guide track 234. The guide track 234 is adjacent the proximal end portion 232 of the driver link 228 and is defined within an area defined by the projection of the pulley disc 224 on to the interior surface of the housing 229. In other words, the guide track 234 does not extend radially beyond the circumference of the pulley disc 224. In the embodiment of FIGS. 2-5, a pin 236 extends generally perpendicular to the longitudinal direction of the driver link 228 through the proximal end portion of the driver link 228 and has one end received in the guide track 234. In this way, motion of the proximal end portion 232 of the driver link 228 is constrained to generally follow the path of the guide track 234 as the pulley disc 224 rotates. In the embodiment of FIG. 3, the drive track 234 has a curved path with a non-constant radial distance from an axis of rotation $A_P$ of the pulley disc 224. The shape of the guide track 234 is chosen such that as the proximal end portion 232 and pin 236 of the driver link 228 generally traverses the path of the guide track 234, the distal end portion 230 of the driver link 228 generally traverses the path of the needle track 214. The shape of the guide track 234 can be chosen based on various other dimensions and desired motion of the needle driver device 200, as discussed in greater detail below.

As shown best in FIGS. 3 and 4, the pin 236 also engages with the pulley disc 224. The pin 236 extends generally perpendicularly to a plane of motion of the driver link to engage the drive track 234 at one end of the pin 236 and a radial slot 238 in the pulley disc 224 at the other end of the pin 236, with the portion of the pin 236 between the two ends extending thorough the driver link 228. Thus, the proximal end portion 232 of the driver link 228 is simultaneously constrained by the pin 236 to follow the guide track 234 and the slot 238 as the pulley disc 224 rotates. Because the radial distance between the guide track 234 and the rotational axis $A_P$ (FIG. 3) of the pulley disc 224 varies along the guide track 234 (i.e., the guide track 234 does not follow a circular arc), the radial slot 238 is provided in the pulley disc 224 to allow radial movement of the proximal end portion 232 of the driver link 228 relative to the rotational axis $A_P$ of the pulley disc 224 as the pulley disc 224 rotates and the pin 236 traverses the guide track 234.

To convert the motion of the proximal end portion 232 of the driver link 228 to reciprocating motion at the distal end portion 230 of the driver link 228 to drive the needle 208 along the needle track 214 as discussed above, motion of the driver link 228 may further be constrained along a central portion 240 of the driver link 228.

With continued reference to FIGS. 3 and 4, a rotatable guide member 242 has a puck configuration with a slot 245 running through the guide member 242 that is transverse to a pinned joint 241 defining a rotational axis $A_B$ of the guide member 242. The rotational axis $A_B$ of the guide member 242 defines a pivot location of the driver link 228. The driver link 228 passes through the slot 245 to operably couple the driver link 228 to the guide member 242 between the proximal and distal end portions of the driver link 228. The driver link 228 can freely slide longitudinally within the slot 245. Thus, the rotational axis $A_B$ of the guide member 242 is not fixed relative to the driver link 228, but the location at which the rotational axis $A_B$ passes through the driver link 228 changes as the driver link 228 translates through the slot 245.

FIG. 5 shows a top view of the needle driver device 200 of FIGS. 3 and 4 taken in a cross-sectional plane parallel to a longitudinal axis of the needle driver device 200 and illustrates how the driver link 228 extends through the guide member 242. As discussed above, the guide member 242 allows translational movement of the driver link 228 along a longitudinal axis $A_L$ of the drive link 228 as the pulley disc 224 rotates and the pin 236 follows the guide track 234, while also constraining the driver link 228 motion such that the longitudinal axis $A_L$ always intersects a fixed point on the housing 229, i.e., an axis of rotation $A_B$ of the guide member 242.

The combination of constraints imparted to movement of the driver link 228 by the guide track 234 and the guide member 242 ensures movement of the distal end portion 230 of the driver link 228 follows the path (e.g., circular arc) defined by the needle track 214. Thus, the distal end portion 230 of the driver link 228 is not directly physically constrained by engagement within or adjacent the needle track 214 to move along the needle track 214, but the constraints on movement of the proximal end portion 232 and central portion of the driver link 228 ensure the movement of the distal end portion 230 follows the needle track 214. In other words, the distal end portion of the driver link 228 is mechanically unconstrained (is a free end of the link 228) but nonetheless follows the needle track 214 due to constraints acting at other locations on the driver link 228.

Such an arrangement can contribute to a relatively small overall size of the needle driver device 200 for a given needle size. In some exemplary embodiments, the needle driver device 200 can be less than 8 mm in diameter, less than 10 mm in diameter, or less than 12 mm in diameter, while accepting relatively larger needle sizes than conventional needle driver devices having similar dimensions. Needle driver devices of the present disclosure can exhibit outside diameters only slightly larger than a needle accepted by the needle driver device. For example, a needle driver device according the present disclosure configured with an 8 millimeter (mm) overall outer diameter could have a needle diameter of only slightly less than 8 mm, such as a diameter greater than 7 mm and less than 8 mm. Likewise, a device with a 10 mm overall outer diameter could have a needle diameter only slightly less than 10 mm, such as a diameter greater than 9 mm and less than 10 mm, a device with a 12 mm overall outer diameter could have a needle diameter only slightly less than 12 mm, such as a diameter greater than 11 mm and less than 10 mm, and so on.

As mentioned above, the shape of the guide track 234 can be chosen such that the path of the guide track 234 and the guide member 242 constrain the motion of the distal end portion 230 of the driver link 228 along the desired path. In exemplary embodiments in which the desired path of the distal end portion 230 of the driver link 228 is a circular arc, the shape of the guide track 234 path does not follow a circular arc, and can be mathematically determined based on the geometries of various drive system components. For example, with continued reference to FIG. 5, the shape of the guide track 234 can be determined as a function of a length L of the driver link 228 between the proximal end portion 232 and the distal end, a distance D from the rotational axis $A_B$ of the guide member 242 to a radius of curvature CN of the circular motion of the needle, a radius R of the curvature of the needle 208, and an engagement angle θ at which the driver link 228 engages the needle 208, as discussed below in connection with FIGS. 6A-6K.

For example, in one embodiment, given the constant parameters D, L, and R discussed above, the shape of the track can be given in a Cartesian plane by the following two equations:

$$X(\theta) = R * \text{Cos}(\theta) + L * \frac{(D - R * \text{Cos}(\theta))}{\sqrt{(R^2 + D^2 - (2 * R * D * \text{Cos}(\theta)))}}$$

$$Y(\theta) = R * \text{Sin}(\theta) * \left(1 - \left(\frac{L}{\sqrt{(R^2 + D^2 - (2 * R * D * \text{Cos}(\theta)))}}\right)\right)$$

Figure 6A:
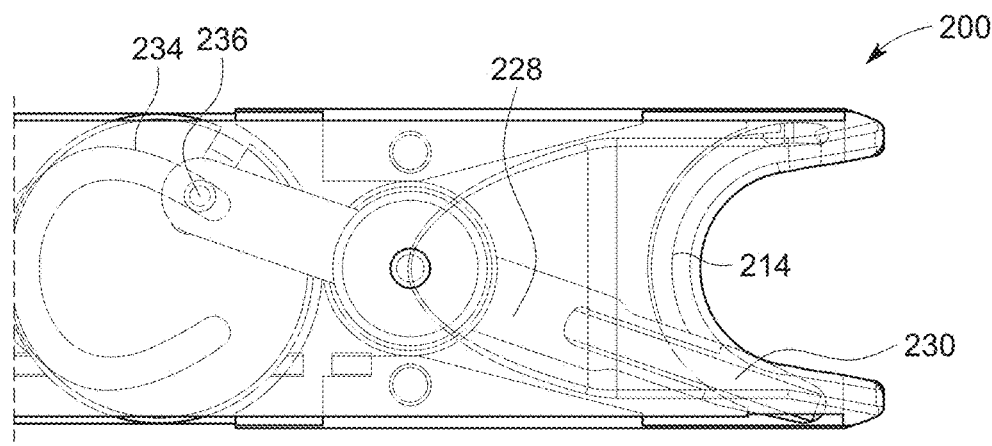
FIG. 6A is a top view of the distal portion of the needle driver device, like the view of FIG. 3, showing the needle and needle driver link of FIG. 2 in an initial configuration.
Figure 6B:
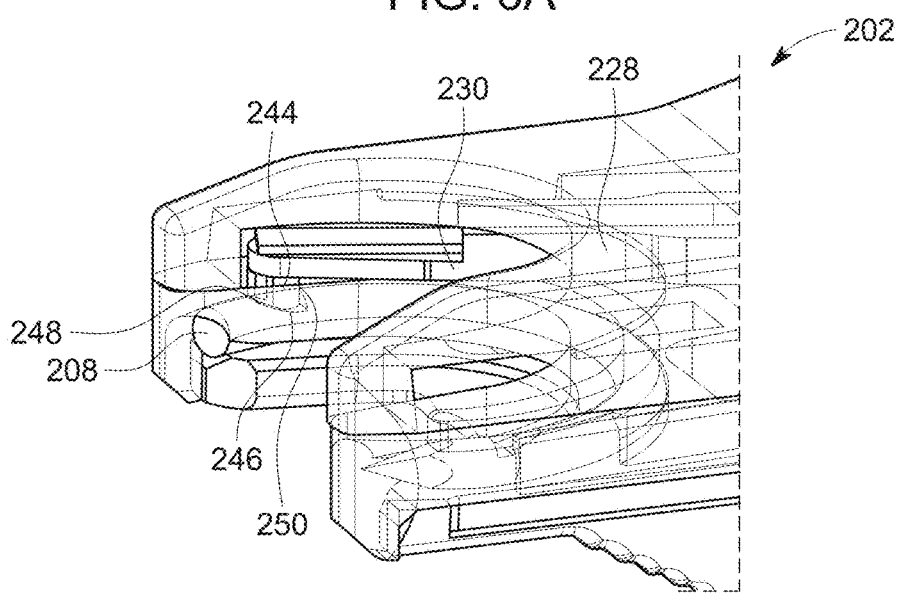
FIG. 6B is a perspective view of the C-shaped portion of the needle driver device, with internal component shown, in the configuration of FIG. 6A.

Operation of the needle driver device 200 of FIGS. 2-5 is shown and described with reference to FIGS. 6A-6K. In FIG. 6A, the driver link 228 is shown in an initial position, with the pin 236 positioned at a first terminus end of the guide track 234 located generally in a first (top, right) quadrant of the pulley disc 224, as viewed in FIG. 6A. The distal end portion 230 of the driver link 228 is positioned at an initial location at the bottom of the guide track 234 as viewed in FIG. 6A. As shown in FIG. 6B, which shows a perspective view of the distal end portion 202 of the needle driver device 200, the distal end portion 230 of the driver link 228 includes a needle engagement member 244 that removably engages the needle 208 to enable the driver link 228 to drive the needle 208 around the needle track 214.

In exemplary embodiments, the needle 208 includes features that interact with the needle engagement member 244. For example, in the embodiment shown in FIGS. 6A-6K, the needle 208 includes a first, ramped notch 246 and second, ramped notch 256 (FIG. 6G). The first notch 246 is located at a proximal end portion of the needle 208 (e.g., an end of the needle 208 opposite the sharp end) and is defined by a ramped upper surface profile 248 terminating in a shoulder portion 250 toward a distal end of the notch 246 (the distal end of the needle 208 being the sharp end). The second notch 256 is located at the distal end portion of the needle 208 (i.e., proximate the sharp end of the needle 208) and is similarly defined with a ramped upper surface profile 258 (FIG. 6G) and a shoulder portion 260 (FIG. 6G). The shoulder portions 250 and 260 allow the needle engagement member 244 to push against the needle 208 to move the needle 208 through the needle track 214, while the ramped surface profiles allow for the disengagement of the needle engagement member 244.

The needle engagement member 244 is configured to engage the needle 208 within the first notch 246 or the second notch 256 as needed to advance the needle 208 around the needle track 234, as discussed further below. In the embodiment of FIGS. 6A-6K, the needle engagement member 244 is a pin coupled to the driver link 228 by a biasing element, such as a leaf spring 252. The leaf spring 252 biases the needle engagement member 244 into contact with the needle 208.

Figure 6C:
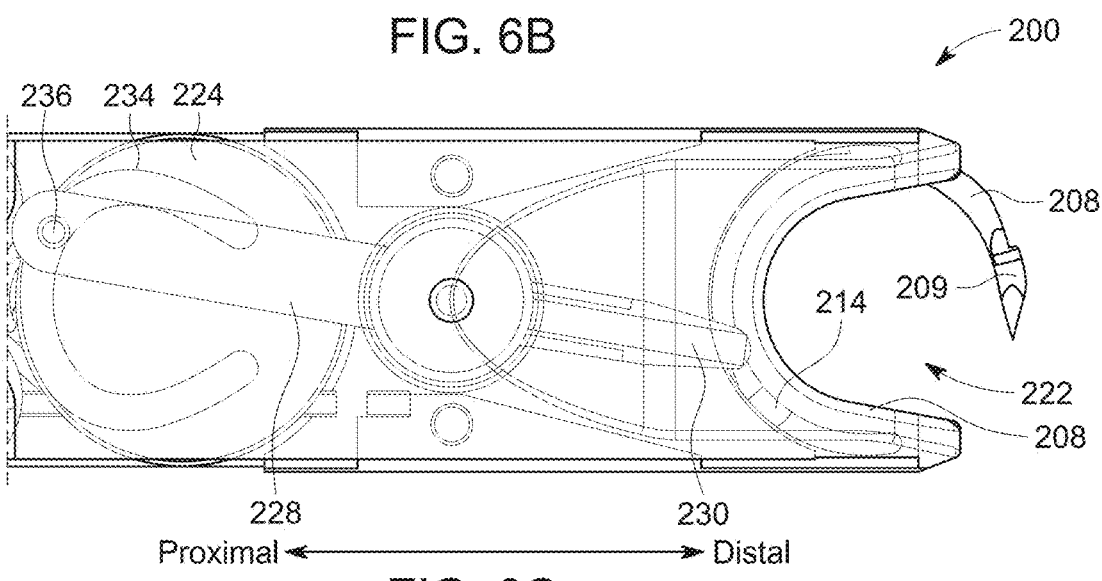
FIGS. 6C and 6D are top views of the distal portion of the needle driver device of FIG. 2 with the needle and needle driver link in various stages of advancement from the initial configuration of FIGS. 6A and 6B.

Referring now to FIG. 6C, as the pulley disc 224 rotates counterclockwise, e.g., based on input from a manipulator (not shown) at the needle driver transmission mechanism, the pin 236 of the driver link 228 advances along the guide track 234, drawing the distal end portion 230 of the driver link 228 along the needle track 214. The needle engagement member 244 (FIG. 6B) engages the needle 208 by bearing against the shoulder portion 250 of the notch 246 of the needle 208 and advances a tip 209 of the needle 208 through the needle track 214 and into the suturing area 222 defined by the C-shaped portion 206. As the pulley disc 224 rotates counterclockwise, resulting movement of the needle driver link 228 causes passive rotation of the guide member 242 about the rotational axis $A_B$, and the needle driver link 228 moves longitudinally within the guide member 242 as its proximal end portion follows the non-circular guide track 234.

Figure 6D:
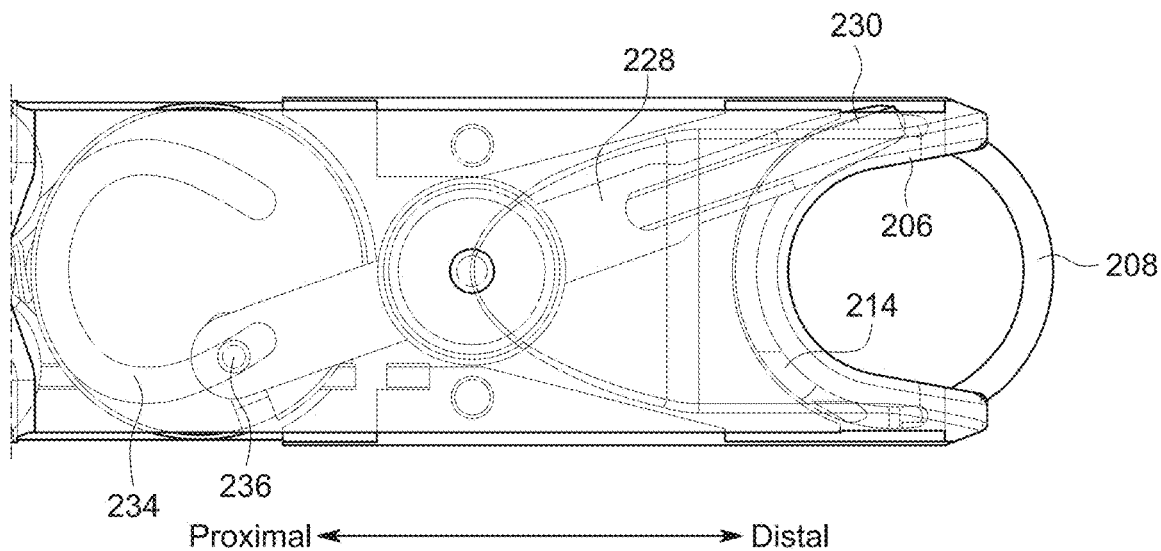
Figure 6E:
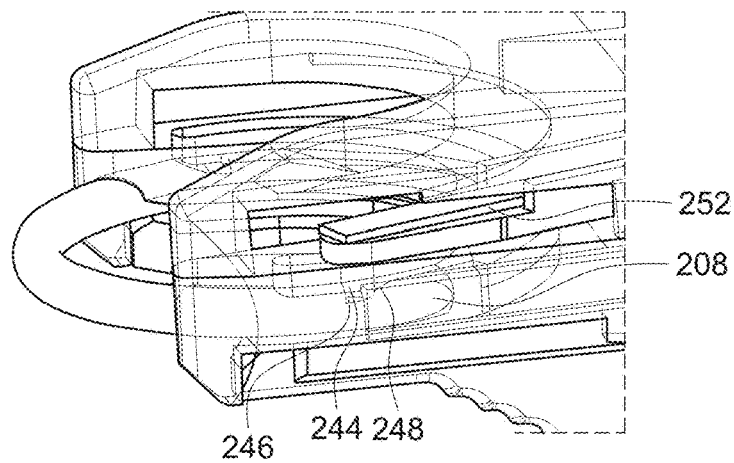
FIGS. 6E-6H are detailed perspective views of the C-shaped portion of the needle driver device in various stages of advancement from the configuration of FIGS. 6C and 6D.
Figure 6F:
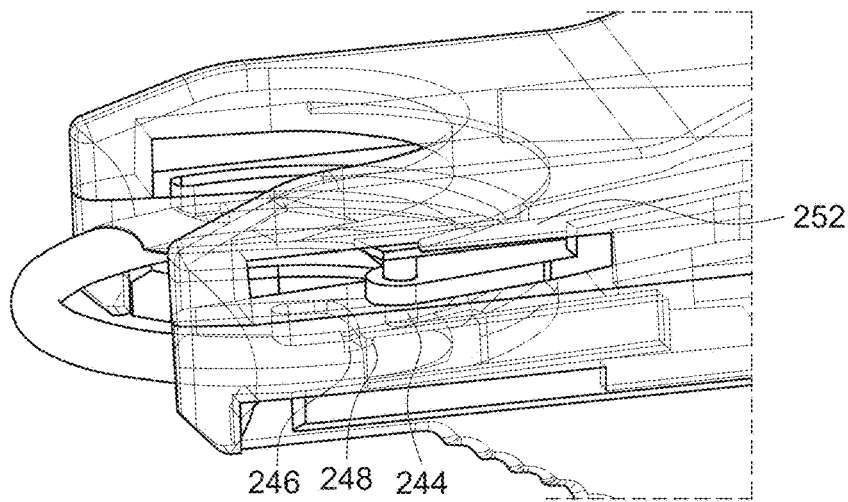
Figure 6G:
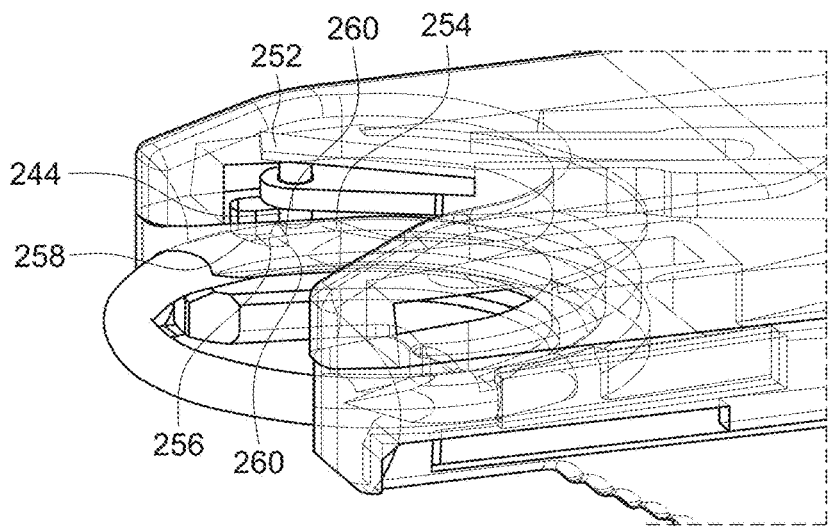
Figure 6H:
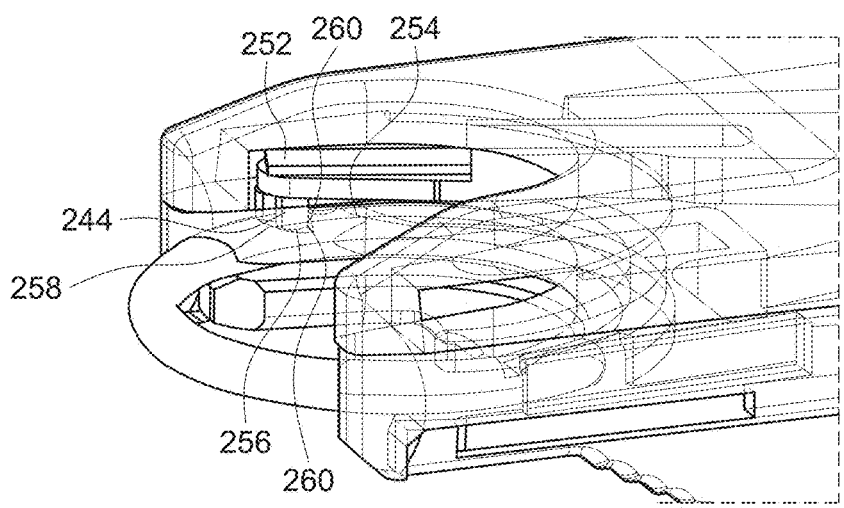

As shown in FIG. 6D, when the pin 236 of the driver link 228 advances to a fourth-quadrant (bottom, right) position in the guide track 234, the distal end portion 230 of the driver link 228 is at an upper position in the needle track 214, and the tip 209 (FIG. 6C) of the needle 208 re-enters the C-shaped portion 206 at an opposite end of the needle track 214. At this point, rotation of the pulley disc 224 is reversed and the pulley disc 224 rotates clockwise, and, as shown in FIGS. 6E and 6F, the needle engagement member 244 rides up the ramped upper surface profile 248 of the notch 246 against force of the leaf spring 252, thereby disengaging from the needle 208. With continued rotation of the pulley disc 224 in the clockwise direction, the distal end portion 230 of the driver link 228 traverses the needle track 214 to the opposite end without moving the needle 208. As shown in FIG. 6G, the needle engagement member 244 rides over a needle ramp 254 against force of the leaf spring 252 and enters the second notch 256 to again engage the needle 208, as shown in FIG. 6H.

Figure 6I:
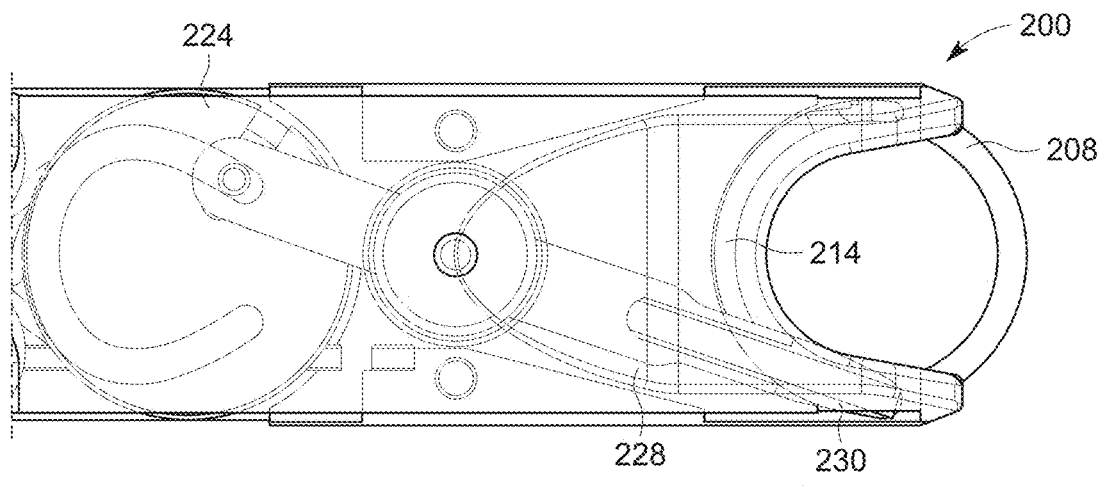
FIGS. 6I-6K are top views of the distal portion of the needle driver device of FIG. 2, with internal components shown, in various stages of advancement from the configuration of FIGS. 6E-6H.
Figure 6J:
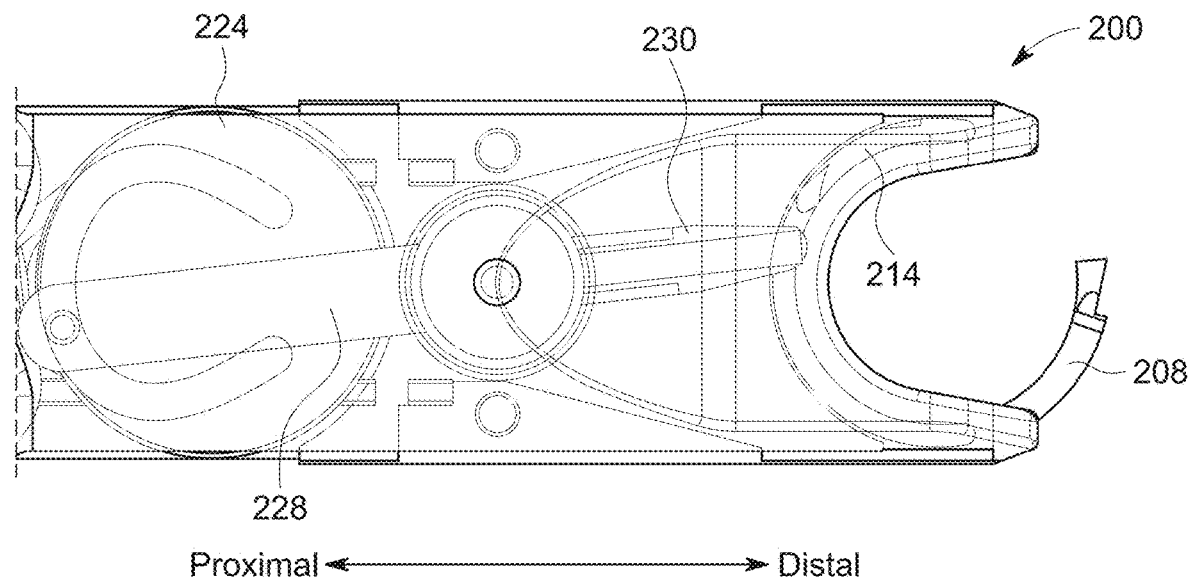
Figure 6K:
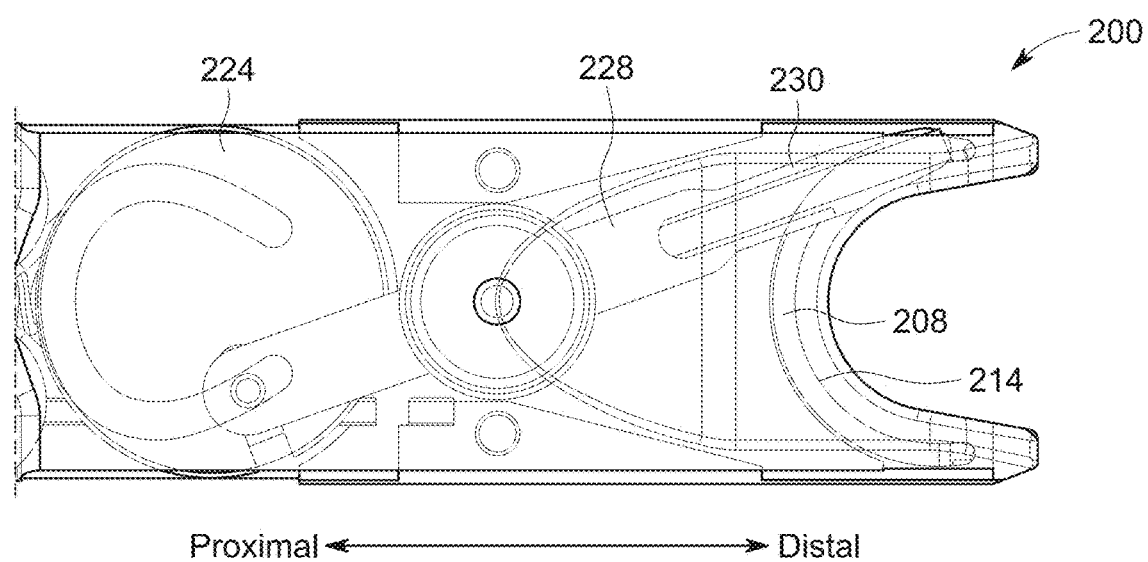

Referring to FIG. 6I, rotation of the pulley disc 224 is again reversed and the pulley disc 224 rotates counterclockwise, moving the distal end portion 230 of the driver link 228 towards the upper (in the view of FIG. 6I) end of the needle track 214. As the pulley disc 224 acts on the proximal end portion 232 of the driver link 228, the driver link 228 and guide member 242 pivot in the housing 229 (FIG. 4). The guide member 242 passively rotates, enabling the driver link 228 to pivot about the rotational axis $A_B$ of the guide member 242. The needle engagement member 244 rests in the second notch 256 and, bearing against the shoulder portion 260 of the second notch 256, draws the needle 208 from the position shown in FIG. 6I, through the position shown in FIG. 6J, and finally to the position shown in FIG. 6K. A subsequent reversal of the rotation of the pulley disc 224, disengagement of the needle engagement member 244 from the second notch 256 of the needle 208, and entry of the needle engagement member 244 in the first notch 246 returns the needle driver device 200 to the initial configuration shown in FIG. 6A, completing a full cycle of the needle driver device 200.

While not illustrated in connection with FIGS. 6A-6K, the needle 208 can be provided with suture material and operation of the needle driver device 200 as discussed in connection with FIGS. 6A-6K can secure suture material in tissue within the suturing area 222 of the C-shaped portion 206 of the needle driver device 200. Moreover, rotation of the pulley disc 224 in the reciprocating rotational directions discussed above can be effectuated automatically, such as by a computer-controlled manipulator to which the transmission mechanism (e.g., 110) of the needle driver device 200 is operably coupled, or can be performed manually, such as in exemplary embodiments in which the needle driver device is configured for use manually (e.g., such as for hand-held operation).

In the embodiment of FIGS. 6A-6K, the needle 208 advances approximately 180 degrees for each continuous stepwise movement of the driver link 228 from one end of the needle track 214 to the opposite end of the needle track 214 or vice versa. That is, a full rotation (360 degrees) of the needle 208 requires two 180-degree rotations in opposite directions of the pulley disc 224 and the associated movements of the driver link 228. The 180-degree increment rotations are non-limiting, and those of ordinary skill in the art would appreciate that in other exemplary embodiments, the needle 208 can be advanced by other amounts per continuous rotational movement of the drive components by increasing the number of equally-spaced notches in the needle 208 and driving the drive components a reduced distance.

Referring now to FIGS. 7-10, another exemplary embodiment of a needle driver device 700 is shown. In this embodiment, each of a proximal end portion, a central portion, and a distal end portion of a needle driver link are constrained in one or more degrees of freedom to ensure the distal end portion of the needle driver link follows a needle track. Unlike the exemplary embodiment of FIGS. 2-5, in which the distal end portion of the needle driver link is free and mechanically unconstrained, the distal end portion of the needle driver link in the exemplary embodiment of FIGS. 7-10 is directly constrained to follow the needle track, as discussed in more detail in connection with FIGS. 9 and 10.

Figure 7:
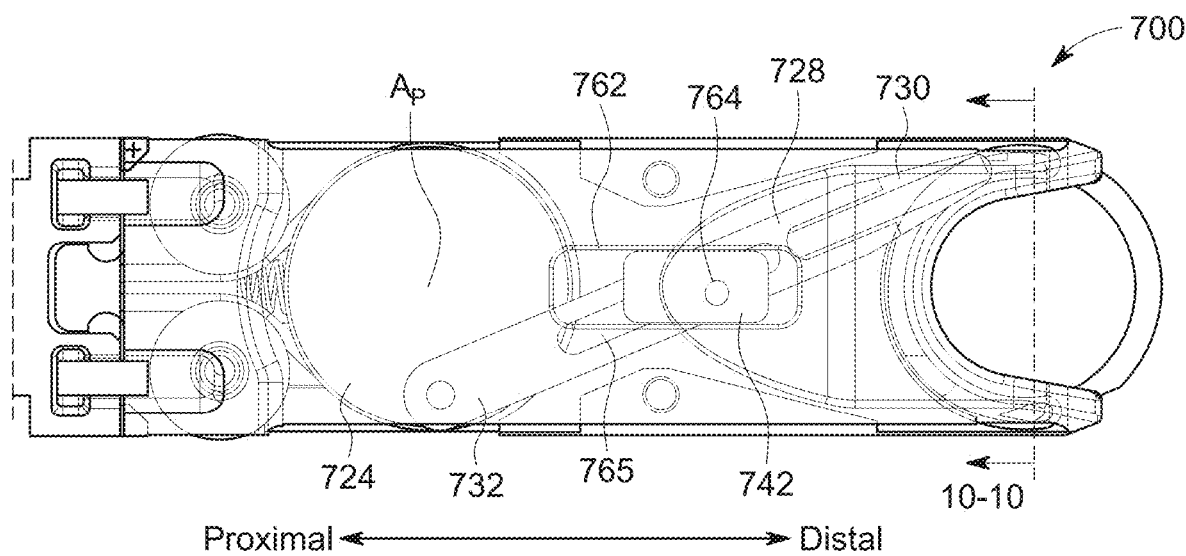
FIG. 7 is a top view of a needle driver device according to another exemplary embodiment of the present disclosure.
Figure 8:
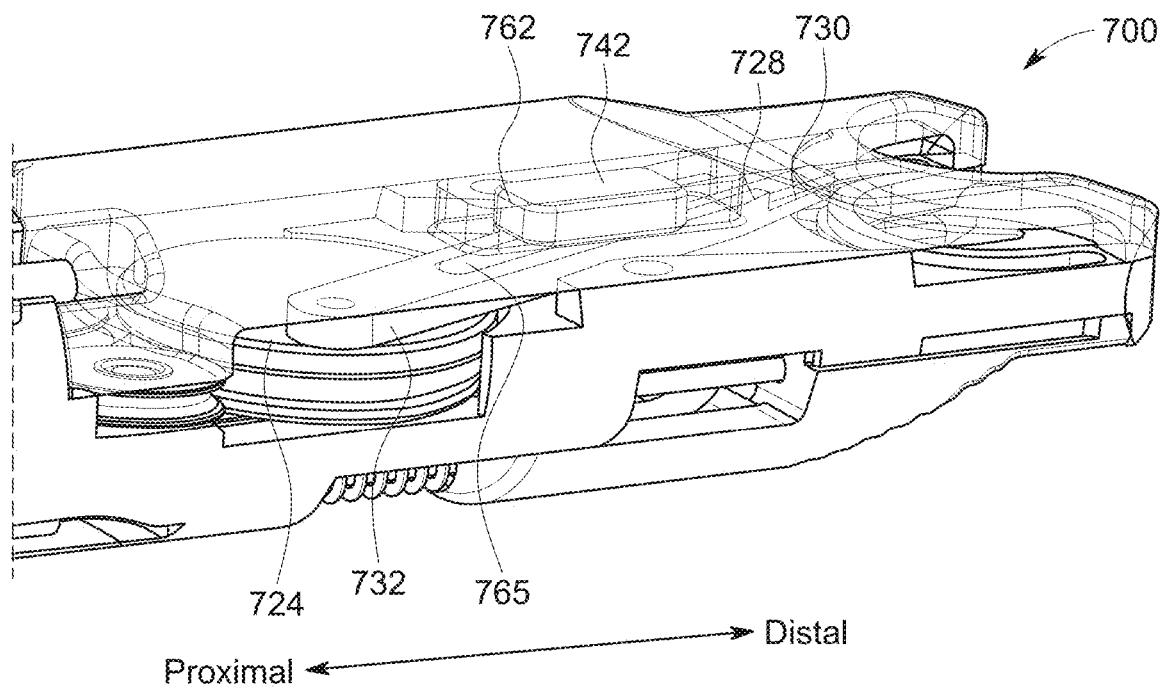
FIG. 8 is a perspective view, with internal components shown, of the needle driver device of FIG. 7.

Referring now to FIGS. 7 and 8, a needle driver device 700 is shown. Many aspects of construction and features of needle driver device 700 are similar to those of needle driver device 200 and are not discussed further. In contrast to the previously described embodiment of the needle driver device 200, the needle driver device 700 includes a driver link 728 having a proximal end portion 732 pinned directly to a rotary drive mechanism, such as a pulley disc 724 of a pulley assembly similar to that described above with reference to FIGS. 3-6, rather than being coupled by a pin that rides in a slot of the pulley disc 224, allowing some relative radial motion of the proximal end portion of the driver link relative to the pulley disc as in the needle driver device 200. Thus, the proximal end portion 732 of the driver link 728 moves with the pulley disc 724 as it rotates so as to follow a circular path at a constant radial distance from a rotational axis $A_P$ of the pulley disc 724. In other words, the motion of the proximal end portion of the driver link 728 is rotational about the rotational axis $A_P$.

The needle driver device 700 further includes a sliding guide member 742 that is free to translate within a guide member track 762. The sliding guide member 742 includes a pin 764 (shown in hidden lines) received in a longitudinal slot 765 provided in the driver link 728. With this configuration, the driver link 728 is rotatable about the pin 764, which defines a pivot location that is simultaneously movable in translation along both a longitudinal axis of the driver link 728 and a longitudinal axis of the needle driver device 700 overall.

Figure 9:
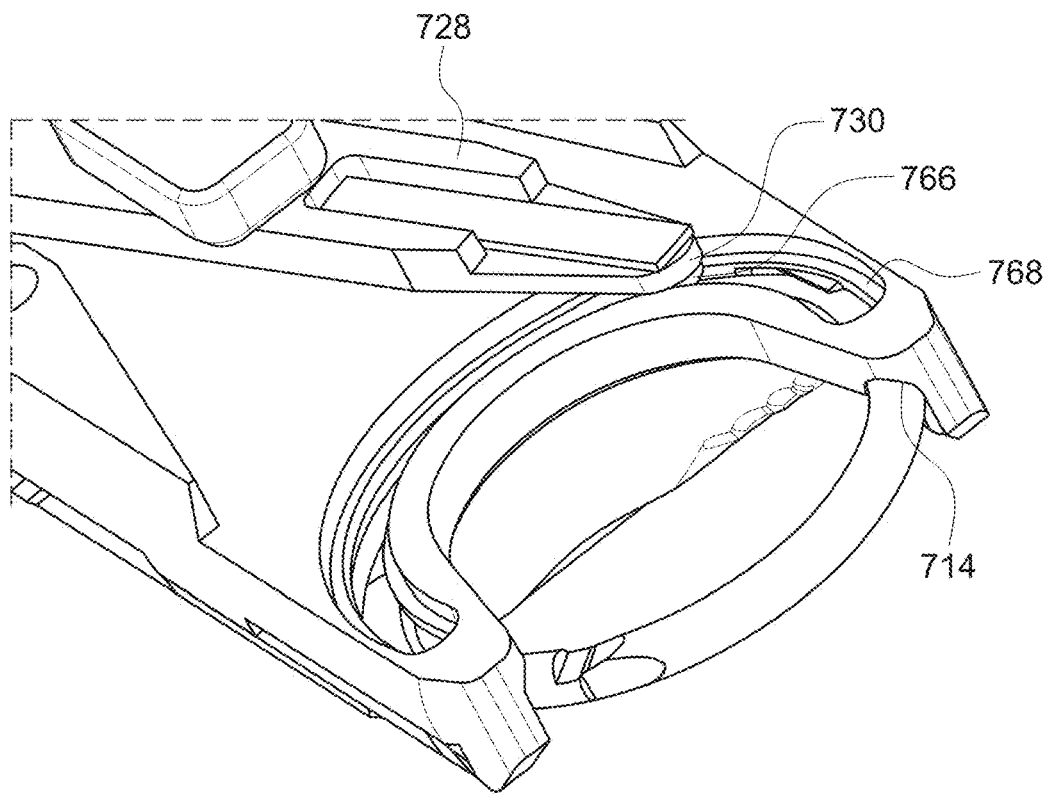
FIG. 9 is a perspective view of the C-shaped portion of the needle driver device of FIG. 7 in a configuration of driving the needle across the opening.
Figure 10:
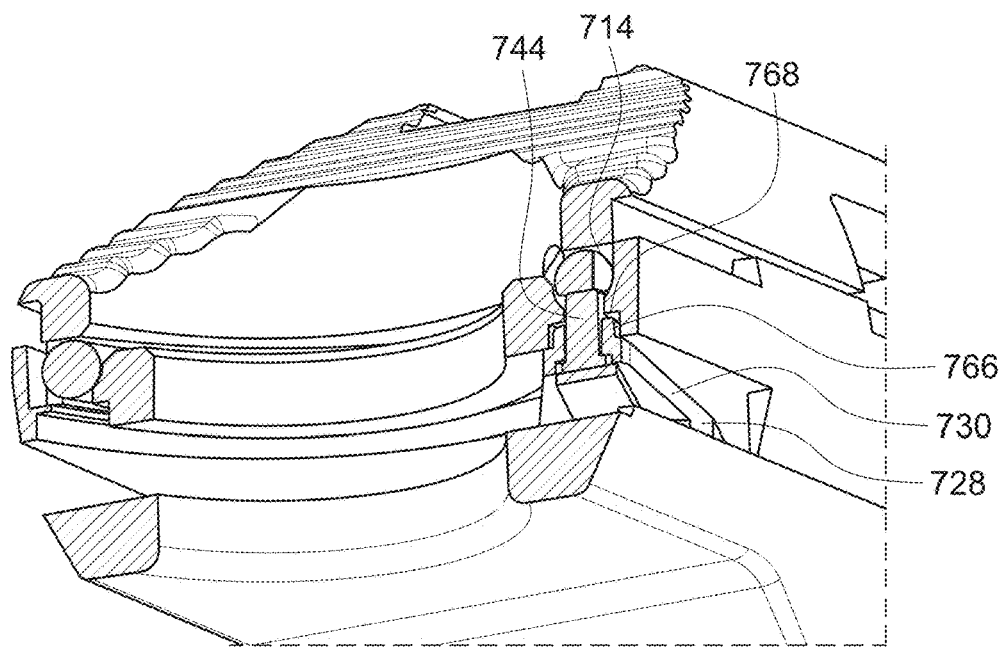
FIG. 10 is a sectional perspective view of the C-shaped portion of the needle driver device of FIG. 7.

Referring now to FIGS. 9 and 10, the distal end portion 730 of the driver link 728 includes a boss 766 that is received within a driver link guide track 768 that is adjacent to, and connected with, a needle track 714. As can be seen in the cross-sectional view of FIG. 10, the driver link guide track 768 and needle track 714 together have a generally "T" shaped cross section, with the horizontal portion of the "T" being the driver link guide track 768 and the vertical portion of the "T" being the needle track 714. The driver link guide track 768 follows a circular arc having a same radius of curvature as the needle track 714. Thus, the motion of both the distal end portion 730 and proximal end portion 732 (FIGS. 7 and 8) of the driver link 728 are constrained along circular arcs, with the pinned connection at the sliding guide member 742 (FIGS. 7 and 8) physically constraining the driver link 728 to rotate about a movable, generally central location on the driver link 728, and the boss 766 physically constraining the distal end portion 730 to move along the driver link guide track 768. The sliding guide member 742 facilitates the desired motion of each of the proximal and distal end portions of the driver link 728, as will be discussed further below in connection with FIGS. 11A-11C.

Figure 11A:
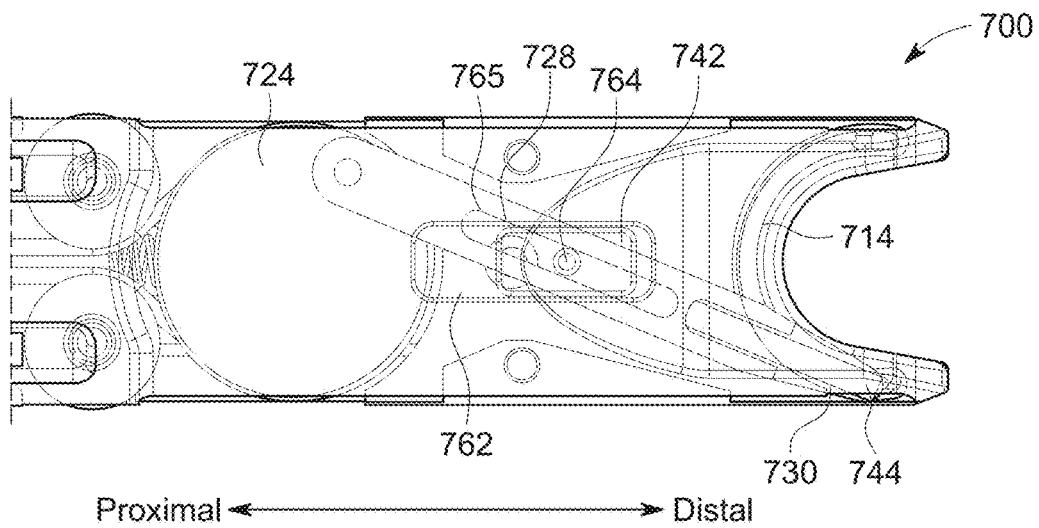
FIGS. 11A-11C are top views of the distal portion of the needle driver device of FIG. 7 showing internal components and various configurations of the needle and needle driver link from an initial configuration through various stages of advancement.
Figure 11B:
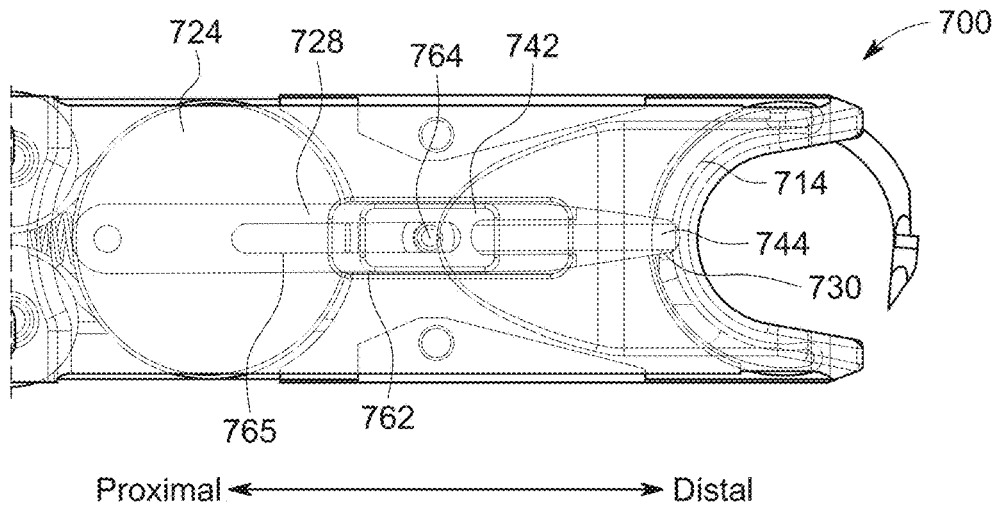
Figure 11C:
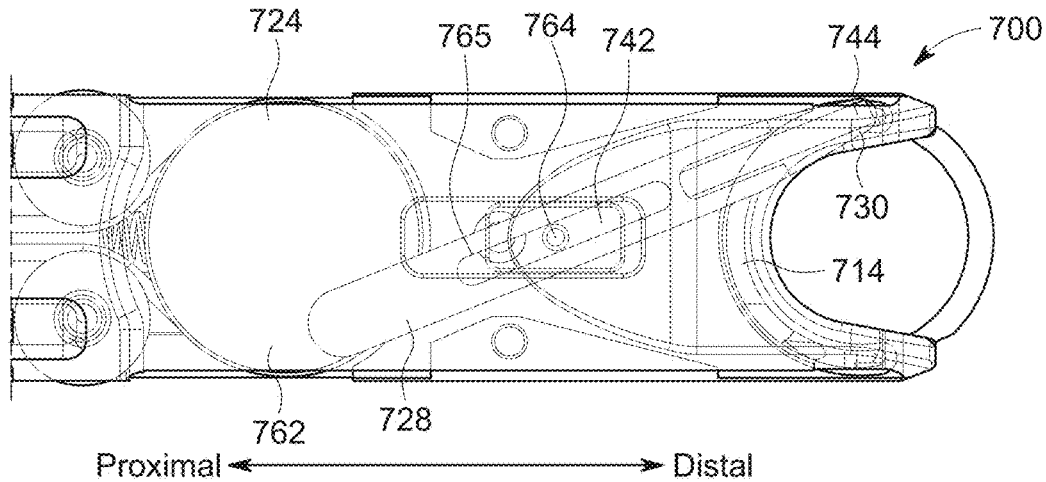

Referring to FIGS. 11A-11C, a partial use cycle of the needle driver device 700 is shown, which has similar aspects as the operation described in connection with FIGS. 6A-6K in that a full rotation of the needle 708 is accomplished by two 180-degree rotations of the pulley disc 724, each of the two rotations being in opposite directions. As described above in connection with FIGS. 6A-6K, however, those of ordinary skill in the art would appreciate that the 180-degree increments of rotation is non-limiting and other increments can be used by adjusting the drive components and cycling of the rotary drive mechanism accordingly.

In FIG. 11A, the needle driver device 700 is shown in an initial position similar to the position of needle driver device 200 shown in FIG. 6A. The driver link 728 comprises a needle engagement member 744 (shown in the cross-sectional view of FIG. 10), which is similar to needle engagement member 244 associated with the embodiment of FIGS. 2-5 and extends through the distal end portion 730 and the boss 766 of the driver link 728 and at least partly into the needle track 714. As the pulley disc 724 rotates counterclockwise, force applied to the pin 764 by the driver link 728 draws the sliding guide member 742 in the proximal direction. Movement of the sliding guide member 742 in the proximal direction enables the distal end portion 730 of the needle driver link to follow a path of the driver link guide track 768, which is along a path parallel to the needle track 714, as best shown in FIG. 10. If the pin 764 were fixed in place relative to the pulley disc 724, the distal end portion 730 of the driver link 728 would be over-constrained in terms of its degree of freedom movement by the pulley disc 724, the pin 764, and the boss 766 (FIGS. 9 and 10). Freedom of the pin 764 to move in the distal and proximal directions, in combination with the longitudinal slot 765 of the driver link 728, enables both the proximal end portion 732 and distal end portion 730 to follow circular arcs throughout their travel.

Referring now to FIG. 11B, as the pulley disc 724 rotates counterclockwise and the distal end portion 730 of the driver link 728 moves clockwise, it drives the needle 708 clockwise along the needle track 714, until it exits the needle track 714 at a distal end of the C-shaped portion 706 and advances into the suturing space defined by the C-shaped portion 706. As shown in FIGS. 10, 11A, and 11B, the driver link 728 includes a needle engagement member 744 that functions similar to the needle engagement member 244 of the embodiment of FIGS. 2-5.

The pin 764 serves to constrain movement of the needle driver link 728. While movement of the needle driver link 728 is nearly fully constrained throughout its movement solely by the constraints on the distal end portion 730 and proximal end portion 732, when the needle driver link 728 is in the position shown in FIG. 11B, movement of the needle driver link 728 can become indeterminate in the absence of the pin 764. As shown in FIG. 11B, the distal end portion 730 of the needle driver link 728 is at a midpoint of the driver link guide track 768 and the proximal end portion 732 of the needle driver link 728 is at a corresponding position halfway through the oscillating rotational movement of the pulley disc 724. Thus, the distal end portion 730 and proximal end portion 732 are aligned along a longitudinal axis of the needle driver device. With continued rotation of the pulley disc 724, for example, in the counterclockwise direction, the distal end portion 730 could either proceed clockwise through the driver link guide track 768, counter to the rotation of the pulley disc 724, or the distal end portion 730 could move in tandem with the proximal end portion 732, such that both the distal end portion 730 and proximal end portion 732 proceed in a counterclockwise rotational direction. In the latter scenario, the needle driver link 728 would move purely in translation. The distal end portion 730 and the proximal end portion 732 would move in tandem until again reaching the position shown in FIG. 11B, at which point movement of the needle driver link 728 would again be indeterminate and the distal end portion 730 and proximal end portion 732 could either move in opposite rotational directions or continue moving in tandem.

The pin 764 forces rotation of the driver link 728 as the pulley disc 724 rotates to advance the driver link 728 from the position shown in FIG. 11B, thereby ensuring the distal end portion 730 and proximal end portion 732 rotate counter to one another. For example, referring now to FIG. 11C, as the pulley disc 724 is rotated counterclockwise further from the position of FIG. 11B, force of the driver link 728 in the angled position shown against the pin 764 pushes the sliding guide member 742 in the distal direction. The needle engagement member 744 engages with and drives the needle 708 further through the needle track 714 until the distal end portion of the needle driver link 728 reaches the position along the driver link guide track 768 opposite its initial position. In this position, the tip 709 of the needle 708 re-enters the needle track 714 at the position of the needle track 714 opposite to where the distal end portion of the needle driver link 728 is located. Further operation of the needle driver device 700 generally follows the sequence shown in connection with FIGS. 6A-6K in terms of rotation of the pulley disc 724 and engagement/disengagement of the needle engagement member 744 with the needle 208. The guide member 742 moves proximally from the distal position shown in FIG. 11C as the needle driver link 728 moves from the position in shown in FIG. 11C back to the position illustrated in FIG. 11A.

As the needle driver link 728 moves in the manner discussed above, at all points in the range of motion of the needle driver link except for the position shown in FIG. 11B, the movement of the needle driver link 728 is fully constrained by the pulley disc 724 and the boss 766 in the needle driver link guide track 768. Further, movement of the needle driver link 728 through the desired range of motion includes simultaneous translation and rotation of the needle driver link 728. The sliding arrangement of the guide member 742 inhibits binding between the driver link 728 and the pinned connection that could otherwise occur if the pinned connection was fixed in place at either the housing or along the driver link 728. That is, because the needle driver link 728 is constrained to follow a circular arc at both the proximal and distal ends, a pinned connection in the center of the needle driver link 728 fixed relative to either the needle driver link 728 or the housing would over-constrain the needle driver link 728 and the needle driver link 728 would be unable to move in the desired motion due to binding of the driver link 728 against the pinned connection. The sliding guide member 742 enables translation of the needle driver link 728 while also forcing rotation of the needle driver link 728 at the point in the range of motion at which the movement of the driver link 728 is indeterminate.

While embodiments of the disclosure discuss rotation of drive components (such as the pulleys 224, 724), portions of the needle driver link, and the needle in clockwise and counterclockwise directions, the particular directions of rotation could be reversed and a person having ordinary skill in the art would understand how such alterations could be accomplished.

Embodiments of the present disclosure provide needle driver devices occupy a relatively small space for a given needle size. Further, embodiments of the disclosure feature fewer parts and potentially greater reliability as compared to conventional designs.

Embodiments described herein may be used, for example, with remotely operated, computer-assisted systems (such, for example, teleoperated surgical systems) such as those described in, for example, U.S. Pat. No. 9,358,074 (filed May 31, 2013) to Schena et al., entitled "Multi-Port Surgical Robotic System Architecture", U.S. Pat. No. 9,295,524 (filed May 31, 2013) to Schena et al., entitled "Redundant Axis and Degree of Freedom for Hardware-Constrained Remote Center Robotic Manipulator", and U.S. Pat. No. 8,852,208 (filed Aug. 12, 2010) to Gomez et al., entitled "Surgical System Instrument Mounting", each of which is hereby incorporated by reference in its entirety. Further, embodiments described herein may be used, for example, with a da Vinci® Surgical System, such as the da Vinci Si® Surgical System (model number IS3000) or the da Vinci Xi® Surgical System, both with or without Single-Site® single orifice surgery technology, all commercialized by Intuitive Surgical, Inc., of Sunnyvale, Calif. Although various embodiments described herein are discussed in connection with a manipulating system of a teleoperated surgical system, the present disclosure is not limited to use with a teleoperated surgical system. Various embodiments described herein can optionally be used in conjunction with hand-held, manual instruments.

Figure 12:
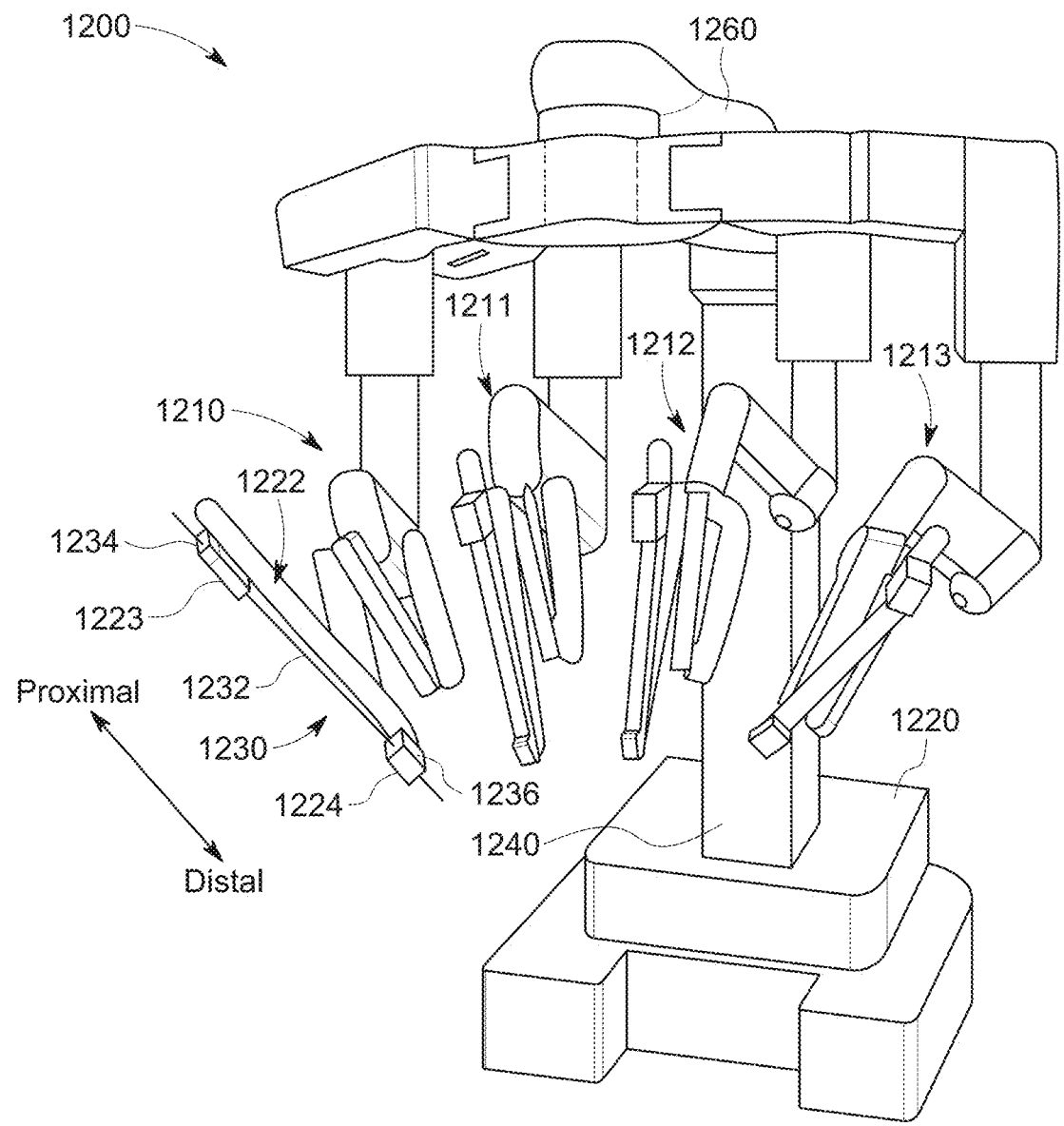
FIG. 12 is a perspective view of a manipulator system according to an exemplary embodiment of the disclosure.

As discussed above, in accordance with various embodiments, surgical instruments of the present disclosure are configured for use in teleoperated, computer-assisted surgical systems employing robotic technology (sometimes referred to as robotic surgical systems). Referring now to FIG. 12, an embodiment of a manipulator system 1200 of a computer-assisted surgical system, to which surgical instruments are configured to be mounted for use, is shown. Such a surgical system may further include a user control system, such as a surgeon console (not shown) for receiving input from a user to control instruments coupled to the manipulator system 1200, as well as an auxiliary system, such as auxiliary systems associated with the DA VINCI SI® and DA VINCI XI®, Da Vinci SP, and Ion systems noted above.

As shown in the embodiment of FIG. 12, a manipulator system 1200 includes a base 1220, a main column 1240, and a main boom 1260 connected to main column 1240. Manipulator system 1200 also includes a plurality of manipulator arms 1210, 1211, 1212, 1213, which are each connected to main boom 1260. Manipulator arms 1210, 1211, 1212, 1213 each include an instrument mount portion 1222 to which an instrument 1230 may be mounted, which is illustrated as being attached to manipulator arm 1210.

Instrument mount portion 1222 comprises a drive assembly 1223 and a cannula mount 1224, with a transmission mechanism 1234 (which may generally correspond to the transmission mechanism 110 discussed in connection with FIG. 1) of the instrument 1230 connecting with the drive assembly 1223, according to an embodiment. Cannula mount 1224 is configured to hold a cannula 1236 through which a shaft 1232 of instrument 1230 may extend to a surgery site during a surgical procedure. Drive assembly 1223 contains a variety of drive and other mechanisms that are controlled to respond to input commands at the surgeon console and transmit forces to the transmission mechanism 1234 to actuate the instrument 1230. Although the embodiment of FIG. 12 shows an instrument 1230 attached to only manipulator arm 1210 for ease of viewing, an instrument may be attached to any and each of manipulator arms 1210, 1211, 1212, 1213.

Figure 13:
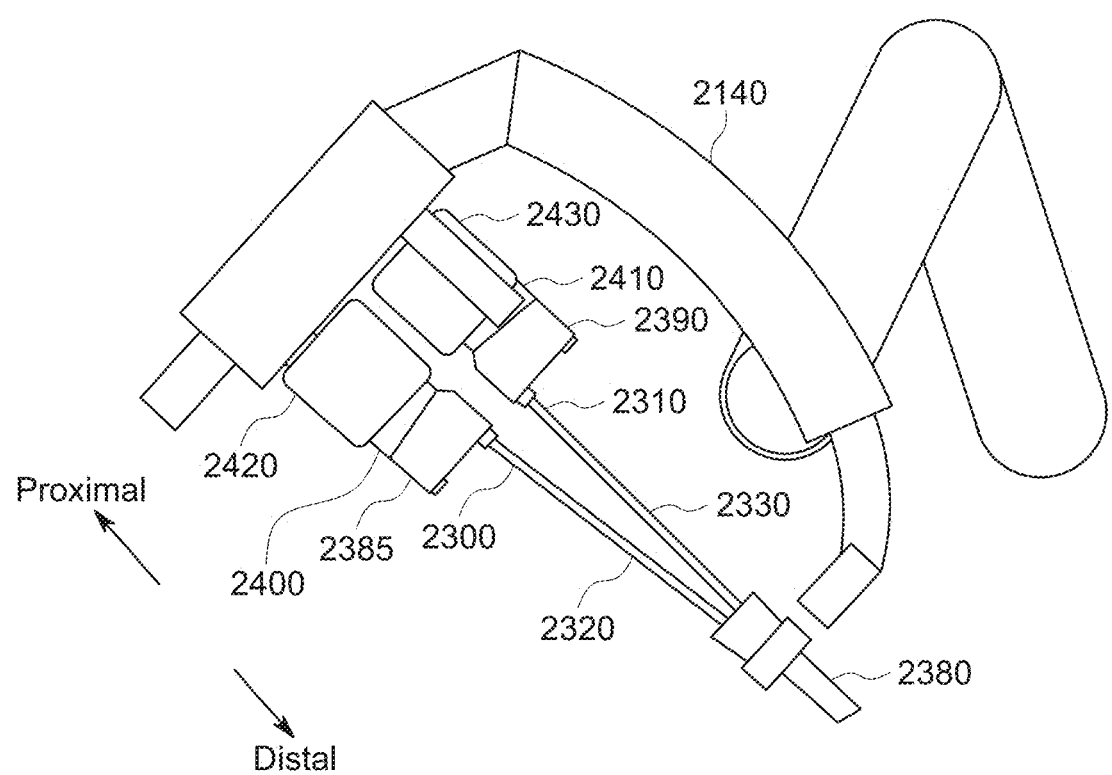
FIG. 13 is a partial schematic view of an embodiment of a manipulator system having a manipulator arm with two instruments in an installed position according to the present disclosure.

Other configurations of surgical systems, such as surgical systems configured for single-port surgery, are also contemplated. For example, with reference now to FIG. 13, a portion of an embodiment of a manipulator arm 2140 of a manipulator system with two surgical instruments 2300, 2310 in an installed position is shown. The surgical instruments 2300, 2310 can generally correspond to instruments discussed above, such as needle driver device 100 disclosed in connection with FIG. 1A. For example, the embodiments described herein may be used with a DA VINCI SP® Surgical System, commercialized by Intuitive Surgical, Inc. of Sunnyvale, Calif. The schematic illustration of FIG. 13 depicts only two surgical instruments for simplicity, but more than two surgical instruments may be mounted in an installed position at a manipulator system as those having ordinary skill in the art are familiar with. Each surgical instrument 2300, 2310 includes a shaft 2320, 2330 that at a distal end has a moveable end effector or an endoscope, camera, or other sensing device, and may or may not include a wrist mechanism (not shown) to control the movement of the distal end.

In the embodiment of FIG. 13, the distal end portions of the surgical instruments 2300, 2310 are received through a single port structure 2380 to be introduced into the patient. As shown, the port structure includes a cannula and an instrument entry guide inserted into the cannula. Individual instruments are inserted into the entry guide to reach a surgical site.

Other configurations of manipulator systems that can be used in conjunction with the present disclosure can use several individual manipulator arms. In addition, individual manipulator arms may include a single instrument or a plurality of instruments. Further, as discussed above, an instrument may be a surgical instrument with an end effector or may be a camera instrument or other sensing instrument utilized during a surgical procedure to provide information, (e.g., visualization, electrophysiological activity, pressure, fluid flow, and/or other sensed data) of a remote surgical site.

Transmission mechanisms 2385, 2390 (which may generally correspond to force transmission mechanism 110 disclosed in connection with FIG. 1) are disposed at a proximal end of each shaft 2320, 2330 and connect through a sterile adaptor 2400, 2410 with drive assemblies 2420, 2430. Drive assemblies 2420, 2430 contain a variety of internal mechanisms (not shown) that are controlled by a controller (e.g., at a control cart of a surgical system) to respond to input commands at a surgeon side console of a surgical system to transmit forces to the force transmission mechanisms 2385, 2390 to actuate surgical instruments 2300, 2310.

The embodiments described herein are not limited to the embodiments of FIG. 12 and FIG. 13, and various other teleoperated, computer-assisted surgical system configurations may be used with the embodiments described herein. The diameter or diameters of an instrument shaft and end effector are generally selected according to the size of the cannula with which the instrument will be used and depending on the surgical procedures being performed.

This description and the accompanying drawings that illustrate various embodiments should not be taken as limiting. Various mechanical, compositional, structural, electrical, and operational changes may be made without departing from the scope of this description and the invention as claimed, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to another embodiment, the element may nevertheless be claimed as included in the other embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

Further modifications and alternative embodiments will be apparent to those of ordinary skill in the art in view of the disclosure herein. For example, the devices and methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with the following claims being entitled to their fullest breadth, including equivalents, under the applicable law.

What is claimed is:

1. A needle driver device, comprising:
    a housing;
    an arc-shaped track in the housing;
    an arc-shaped needle configured to be received in the arc-shaped track, the arc-shaped needle moveable along a curved path comprising the arc-shaped track;
    a rotary drive mechanism in the housing;
    a needle driver link in the housing, the needle driver link comprising:
        a distal end portion configured to removably engage the arc-shaped needle; and
        a proximal end portion coupled to the rotary drive mechanism; and
    a guide member in the housing and coupled to and configured to guide motion of the needle driver link, the guide member defining a pivot location of the needle driver link between the distal end portion and the proximal end portion of the needle driver link, the pivot location being fixed relative to the housing,
    wherein the needle driver link is rotatable about the pivot location, and
    wherein the guide member is rotatable about the pivot location in response to movement of the needle driver link.

2. The needle driver device of claim 1, wherein the guide member comprises a slot dimensioned to receive a portion of the needle driver link.

3. The needle driver device of claim 1, wherein the pivot location is movable along the needle driver link in response to movement of the needle driver link.

4. The needle driver device of claim 1, wherein the proximal end portion of the needle driver link is coupled to the rotary drive mechanism by a pin.

5. The needle drive device of claim 4, wherein the rotary drive mechanism comprises a radially extending slot in which the pin is received.

6. The needle driver device of claim 1, wherein the rotary drive mechanism is operably coupled with an input drive configured to drive the rotary drive mechanism in an oscillating rotational motion.

7. The needle driver device of claim 1, wherein the distal end portion of the needle driver link comprises a needle engagement member configured to releasably engage the arc-shaped needle.

8. The needle driver device of claim 7, further comprising a biasing element arranged to exert a biasing force on the distal end portion of the needle driver link in a state of the needle engagement member being engaged with the arc-shaped needle, the biasing force acting to bias the needle engagement member into engagement with the arc-shaped needle.

9. A needle driver device, comprising:
    an arc-shaped track;
    an arc-shaped needle configured to be received in the arc-shaped track, the arc-shaped needle moveable along a curved path comprising the arc-shaped track;
    a rotary drive mechanism;
    a needle driver link, comprising:
        a distal end portion configured to removably engage the arc-shaped needle; and
        a proximal end portion coupled to the rotary drive mechanism; and
    a guide member coupled to the needle driver link and configured to guide motion of the needle driver link, the guide member defining a pivot location of the needle driver link between the distal end portion and the proximal end portion of the needle driver link,
    wherein the needle driver link is rotatable about the pivot location,
    wherein the guide member is moveable in response to movement of the needle driver link, and
    wherein the needle driver link is constrained to move through the guide member in a longitudinal direction of the needle driver link.

10. The needle driver device of claim 9, wherein the pivot location is movable relative to the rotary drive mechanism.

11. A needle driver device, comprising:
    an arc-shaped track;
    an arc-shaped needle configured to be received by the arc-shaped track, the arc-shaped needle moveable along a path comprising the arc-shaped track;
    a rotary drive mechanism; and
    a needle driver link comprising:
        a distal end portion removably engageable with the arc-shaped needle and configured to be removably coupled to the arc-shaped track; and
        a proximal end portion coupled to the rotary drive mechanism and constrained to engage with and follow a curved, non-circular path defined by a track in response to rotation of the rotary drive mechanism.

12. The needle driver device of claim 11, further comprising a guide member coupled to the needle driver link between the proximal end portion and the distal end portion of the needle driver link, the guide member configured to guide motion of the needle driver link.

13. The needle driver device of claim 12, wherein the needle driver link is moveable linearly along a longitudinal direction of the needle driver link through the guide member.

14. The needle driver device of claim 11, wherein the proximal end portion of the needle driver link is coupled to the rotary drive mechanism by a pin.

15. The needle driver device of claim 14, wherein the rotary drive mechanism comprises a radially extending slot in which the pin is received.

* * * * *